US008889622B2

(12) United States Patent
Thio et al.

(10) Patent No.: US 8,889,622 B2
(45) Date of Patent: Nov. 18, 2014

(54) METHODS OF INHIBITING SEIZURE IN A SUBJECT

(75) Inventors: Kwee Liu Lin Thio, St. Louis, MO (US); Kelvin A. Yamada, St. Louis, MO (US)

(73) Assignee: Washington University, St. Louis, MO (US)

( * ) Notice: Subject to any disclaimer, the term of this patent is extended or adjusted under 35 U.S.C. 154(b) by 935 days.

(21) Appl. No.: 12/179,856

(22) Filed: Jul. 25, 2008

(65) Prior Publication Data

US 2009/0281522 A1 Nov. 12, 2009

Related U.S. Application Data

(60) Provisional application No. 60/951,793, filed on Jul. 25, 2007.

(51) Int. Cl.
*A61P 3/04* (2006.01)
*A61K 38/26* (2006.01)
*G01N 33/48* (2006.01)
*A61K 38/22* (2006.01)
*A61K 31/00* (2006.01)

(52) U.S. Cl.
CPC ............. *A61K 38/2264* (2013.01); *A61K 31/00* (2013.01)
USPC ........... 514/11.7; 506/10; 514/17.7; 435/375; 702/19

(58) Field of Classification Search
None
See application file for complete search history.

(56) References Cited

U.S. PATENT DOCUMENTS

| | | | |
|---|---|---|---|
| 5,399,346 A | | 3/1995 | Anderson et al. |
| 5,521,283 A | * | 5/1996 | DiMarchi et al. ............. 530/324 |
| 5,532,336 A | * | 7/1996 | DiMarchi et al. ............. 530/324 |
| 5,589,466 A | | 12/1996 | Felgner et al. |
| 5,804,413 A | | 9/1998 | DeLuca et al. |
| 6,106,826 A | | 8/2000 | Brandt et al. |
| 6,777,388 B1 | | 8/2004 | Grasso et al. |
| 6,818,209 B1 | | 11/2004 | Mitrophanous et al. |
| 6,936,272 B2 | | 8/2005 | Martin et al. |
| 7,186,691 B2 | | 3/2007 | Quay et al. |
| 7,208,572 B2 | | 4/2007 | Grasso et al. |
| 7,232,899 B2 | | 6/2007 | Von Seggern et al. |

FOREIGN PATENT DOCUMENTS

| | | |
|---|---|---|
| WO | 9746585 A2 | 12/1997 |
| WO | 9919330 A1 | 11/2008 |

OTHER PUBLICATIONS

Erickson et al., Nature, 381:415-418, May 30, 1996.*
Fliedner et al. Endocrinology, 147(5):2088-2094, (2006).*
Yang et al., Epilepsia, 47:240-241, Abstract #3.106, published Oct. 30, 2006.*
Barnabe-Heider et al, Evidence that Embryonic Neurons Regulate the Onset of Cortical Gliogenesis via Cardiotrophin-1, Neuron, 2005, pp. 253-265. vol. 48.
Bjorbek et al, Leptin Signaling in the Central Nervous System and the Periphery, Recent Prog Horm Res, 2004, pp. 305-331, vol. 59.
Boado et al, Drug Delivery of Antisense Molecules to the Brain for Treatment of Alzheimer's Disease and Cerebral AIDS, J Pharm. Sci, 1998, pp. 1308-1315, vol. 87, No. 11.
Chen et al, Evidence That the Diabetes Gene Encodes the Leptin Receptor: Identification of a Mutation in the Leptin Receptor Gene in db/db mice, Cell, 1996, pp. 491-495, vol. 84.
Dicou et al, Neuroprotective effects of leptin in vivo and in vitro, Neurochemistry, 2001, pp. 3947-3951, vol. 12, No. 18.
Edge et al, Total synthesis of a human leukocyte interferon gene, Nature, pp. 756-762, vol. 292, (1981).
Fruhbeck, G, Intracellular signalling pathways activated by leptin, Biochem J., 2006, pp. 7-20. vol. 393.
Goins et al, Herpes Simplex Virus Type 1 Vector-Mediated Expression of Nerve Growth Factor Protects Dorsal Root Ganglion Neurons from Peroxide Toxicity, J Virology, 1999, pp. 519-532, vol. 73, No. 1.
Goodkin et al, Status Epilepticus Increases the Intracellular Accumulation of GABAa Receptors, J Neurosci, 2005, pp. 5511-5520. vol. 25, No. 23.
Gossen et al, Transcriptional Activation by Tetracyclines in Mammalian Cells, Science, 1995, pp. 1766-1769, vol. 268.
Gossen et al, Tight control of gene expression in mammalian cells by tetracycline-responsive promoters, PNAS, 1992, pp. 5547-5551, vol. 89.
Hsu et al, Leptin Interferes with Adrenocorticotropin/3', 5' -Cyclic Adenosine Monophosphate (cAMP) Signaling, Possibly through a Janus Kinase 2-Phosphatidylinositol 3-Kinase/Akt-Phosphodiesterase 3-cAMP Pathway, to Down-Regulate Cholesterol Side-Chain Cleavage Cytochrome P450 Enzyme in Human Adrenocortical NCI-H295 Cell Line, J. Clin. Endocrinology and Metabolism, 2006, pp. 2761-2769, vol. 91.
Jay et al, Chemical Synthesis of a Biologically Active Gene for Human Immune Interferon-γ, J Biol Chem, 1984, pp. 6311-6317, vol. 259, No. 10.
Khaliq et al, Relatve Contributions of Axonal and Somatc Na Channes to Action Potential Initation in Cerebellar Purkinje Neurons, J Neurosci, 2006, pp. 1935-1944, vol. 26, No. 7.
Liu et al, Herpes Simplex Virus Mediated Gene Transfer to Primate Ocular Tissues, Exp Eye Res, 1999, pp. 385-395, vol. 69.
Mangan et al, Factors Underying Burstng Behavior in a Network of Cultured Hippocampal Neurons Exposed to Zero Magnesium, J. Neurophysiol, 2004, pp. 946-957, vol. 91.
Morris et al, A new peptide vector for efficient delivery of oligonucleotides into mammalian cells, Nucleic Acids Research, 1997, pp. 2730-2736, vol. 25, No. 14.
Nambair et al, Total Synthesis and Cloning of a Gene Coding for the Ribonuclease S Protein, Science, 1984, pp. 1299-1301, vol. 223.
OMalley et al, Leptin-induced dynamic changes in the actin cytoskeleton mediate the activation and synaptic clustering of BK channels, FASEB J, 2005, pp. 1917-1919, vol. 19.
Qiu et al, Conditioning Injury-Induced Spinal Axon Regeneration Requires Signal Transducer and Activator of Transcription 3 Activation, J Neurosci, 2005, pp. 1645-1653, vol. 25, No. 7.

(Continued)

*Primary Examiner* — Daniel E Kolker
*Assistant Examiner* — Stacey N MacFarlane
(74) *Attorney, Agent, or Firm* — Polsinelli PC

(57) ABSTRACT

The present invention relates to methods of inhibiting seizure in a subject. In particular, the invention provides methods of increasing brain leptin levels in a subject.

7 Claims, 17 Drawing Sheets

(56) References Cited

OTHER PUBLICATIONS

Roger et al, Distinctive characteristics of frontal lobe epilepsy versus idiopathic generalized epilepsy, Adv Neurol, 1992, pp. 399-410, vol. 57.

Rossi, JJ Therapeutic antisense and ribozymes, Br Med Bull, 1995, pp. 217-25, vol. 51, No. 1.

Rossi et al, Recent advances in inducible gene expression systems, Curr Opin Biotechnol, 1998, pp. 451-456, vol. 9.

Rozhavskaya-Arena et al, Design of a Synthetic Leptin Agonist: Effects on Energy Balance, Glucose Homeostasis, and Thermoregulation, Endocrinology, 2000, pp. 2501-2507. vol. 141.

Russo et al, Antiapoptotic Effects of Leptin in Human Neuroblastoma Cells, Endocrinology, 2004, pp. 4103-4112, vol. 145, No. 9.

Samson et al, A 35 Amino Acid Fragment of Leptin Inhibits Feeding in The Rat, Endocrinology, 1996, pp. 5182-5185, vol. 137, No. 11.

Scheffer et al, Generalized epilepsy with febrile seizures plus A genetic disorder with heterogeneous clinical phenotypes, Brain, 1997, pp. 479-490, vol. 120.

Shanley et al, Leptin Enhances NMDA Receptor Function and Modulates Hippocampal Synaptic Plasticity, J Neurosci, 2001, pp. 1-6. vol. 21, No. RC186.

Shanley et al, Leptin inhibits epileptiform-like activity in rat hippocampal neurones via PI 3-kinase-driven activation of BK channels, J of Physiology, 2002, pp. 933-944, vol. 545.3.

Shimizu et al, Inhibition of appetite by nasal leptin administration in rats, Int J Obes Relat Metab /Disord, 2005, pp. 858-863, vol. 29.

Singh et al, Generalized Epilepsy with Febrile Seizures Plus: A Common Childhood-Onset Genetic Epilepsy Syndrome, Ann Neurol, 1999, pp. 75-81, vol. 45.

Stables et al, Models for Epilepsy and Epileptogenesis: Report from the NIH Workshop, Bethesda, Maryland, Epilepsia, 2002, pp. 1410-1420, vol. 43, No. 11.

Thio et al, Benzodiazepines Block α2-Containing Inhibitory Glycine Receptors in Embryonic Mouse Hippocampal Neurons, J Neurophysiol, 2003, pp. 89-99, vol. 90.

Thio et al, Leptin Contributes to Slower Weight Gain in Juvenile Rodents on a Ketogenic Diet, Pediatric Res, 2006, pp. 413-417, vol. 60, No. 4.

Thio et al, Ketone bodies do not directly alter excitatory or inhibitory hippocampal synaptic transmission, Neurology, 2000, pp. 325-331, vol. 54, No. 2.

Wong et al, Impaired Glial Glutamate Transport in a Mouse Tuberous Sclerosis Epilepsy Model, Ann Neurol, 2003, pp. 251-256, vol. 54.

Xu et al, Viral transduction of trkA into cultured nodose and spinal motor neurons conveys NGF responsiveness, Dev Biol. 1994, pp. 152-161. vol. 163, No. 1.

Xu et al, Leptin inhibits 4-aminopyridine- and pentylenetetrazole-induced seizures and AMPAR-mediated synaptic transmission in rodents, J Clin Invest, 2008, pp. 272-280, vol. 118, No. 1.

Yadav et al, JAK/STA3 Pathway Is Involved in Survival of Neurons in Response to Insulin-like Growth Factor and Negatively Regulated by Suppressor of Cytokine Signaling-3, J Biol Chem, 2005, pp. 31830-31840, vol. 280, No. 36.

Yang et al, Focal Cooling Rapidly Terminates Experimental Neocortical Seizures, Ann Neurol, 2001, pp. 721-726, vol. 49.

Ayyildiz, "The effect of leptin on penicillin-induced epileptiform activity in rats", Brain Research Bulletin, 2006, pp. 374-378, vol. 68.

\* cited by examiner

SEQ ID NO: 1

Ser Cys His Leu Pro Xaa Ala Ser Gly Leu Glu Thr Leu Asp Ser
 1               5                  10                  15
Leu Gly Gly Val Leu Glu Ala Ser Gly Tyr Ser Thr Glu Val Val
                20                  25                  30
Ala Leu Ser Arg Leu Xaa Gly Ser Leu Xaa Asp Xaa Leu Xaa Xaa
                35                  40                  45
Leu Asp Leu Ser Pro Gly Cys
                50

FIG. 10

SEQ ID NO: 2

```
1                   5                   10                  15
Ile Pro Gly Leu His Pro Ile Leu Thr Leu Ser Lys Xaa Asp Xaa
                    20                  25                  30
Thr Leu Ala Val Tyr Xaa Xaa Ile Leu Thr Ser Xaa Pro Ser Arg
                    35                  40                  45
Xaa Val Ile Xaa Ile Ser Xaa Asp Leu Xaa Leu Arg Asp Leu
                    50                  55                  60
Leu His Val Leu Ala Phe Ser Lys Ser Cys His Leu Pro Xaa Ala
                    65                  70                  75
Ser Gly Leu Glu Thr Leu Asp Ser Leu Gly Gly Val Leu Glu Ala
                    80                  85                  90
Ser Gly Tyr Ser Thr Glu Val Val Ala Leu Ser Arg Leu Xaa Gly
                    95                  100                 105
Ser Leu Xaa Asp Xaa Leu Xaa Xaa Leu Asp Leu Ser Pro Gly Cys
```

FIG. 11

SEQUENCE LISTING

```
<160> NUMBER OF SEQ ID NOS: 13

<210> SEQ ID NO 1
<211> LENGTH: 52
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: X may be Trp or Gln
<220> FEATURE:
<221> NAME/KEY: MISC_FEATURE
<222> LOCATION: (36)..(36)
<223> OTHER INFORMATION: X may be Gln or Glu
<220> FEATURE:
<221> NAME/KEY: MISC_FEATURE
<222> LOCATION: (40)..(40)
<223> OTHER INFORMATION: X may be Gln or Glu
<220> FEATURE:
<221> NAME/KEY: MISC_FEATURE
<222> LOCATION: (42)..(42)
<223> OTHER INFORMATION: X may be Ile, Leu, Met or methionine sulfoxide
<220> FEATURE:
<221> NAME/KEY: MISC_FEATURE
<222> LOCATION: (44)..(44)
<223> OTHER INFORMATION: X may be Gln or Glu
<220> FEATURE:
<221> NAME/KEY: misc_feature
<222> LOCATION: (45)..(45)
<223> OTHER INFORMATION: Xaa can be any naturally occurring amino acid

<400> SEQUENCE: 1
```

```
Ser Cys His Leu Pro Xaa Ala Ser Gly Leu Glu Thr Leu Asp Ser Leu
1               5                   10                  15

Gly Gly Val Leu Glu Ala Ser Gly Tyr Ser Thr Glu Val Val Ala Leu
            20                  25                  30

Ser Arg Leu Xaa Gly Ser Leu Xaa Asp Xaa Leu Xaa Xaa Leu Asp Leu
        35                  40                  45

Ser Pro Gly Cys
    50
```

<210> SEQ ID NO 2
<211> LENGTH: 105
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: X may be Ile, Leu, Met or methionine sulfoxide
<220> FEATURE:
<221> NAME/KEY: MISC_FEATURE
<222> LOCATION: (15)..(15)
<223> OTHER INFORMATION: X may be Gln or Glu
<220> FEATURE:
<221> NAME/KEY: MISC_FEATURE
<222> LOCATION: (21)..(21)
<223> OTHER INFORMATION: X may be Gln or Glu
<220> FEATURE:
<221> NAME/KEY: MISC_FEATURE
<222> LOCATION: (22)..(22)
<223> OTHER INFORMATION: X may be Gln or Glu
<220> FEATURE:
<221> NAME/KEY: MISC_FEATURE
<222> LOCATION: (27)..(27)
<223> OTHER INFORMATION: X may be Ile, Leu, Met or methionine sulfoxide
<220> FEATURE:
<221> NAME/KEY: MISC_FEATURE
<222> LOCATION: (31)..(31)
<223> OTHER INFORMATION: X may be Asn, Asp, or Gln
<220> FEATURE:
<221> NAME/KEY: MISC_FEATURE
<222> LOCATION: (34)..(34)
<223> OTHER INFORMATION: X may be Gln or Glu
<220> FEATURE:
<221> NAME/KEY: MISC_FEATURE
<222> LOCATION: (37)..(37)
<223> OTHER INFORMATION: X may be Asn, Asp, or Gln
<220> FEATURE:
<221> NAME/KEY: MISC_FEATURE
<222> LOCATION: (41)..(41)
<223> OTHER INFORMATION: X may be Asn, Asp or Gln
<220> FEATURE:
<221> NAME/KEY: MISC_FEATURE
<222> LOCATION: (59)..(59)
<223> OTHER INFORMATION: X may be Trp or Gln
<220> FEATURE:
<221> NAME/KEY: MISC_FEATURE
<222> LOCATION: (89)..(89)
<223> OTHER INFORMATION: X may be Gln or Glu
<220> FEATURE:
<221> NAME/KEY: MISC_FEATURE
<222> LOCATION: (93)..(93)
<223> OTHER INFORMATION: X may be Gln or Glu
<220> FEATURE:
<221> NAME/KEY: MISC_FEATURE
<222> LOCATION: (95)..(95)
<223> OTHER INFORMATION: X may be Ile, Leu, Met or methionine sulfoxide
<220> FEATURE:
<221> NAME/KEY: MISC_FEATURE
<222> LOCATION: (97)..(97)
<223> OTHER INFORMATION: X may be Trp or Gln
<220> FEATURE:
<221> NAME/KEY: MISC_FEATURE
<222> LOCATION: (98)..(98)
<223> OTHER INFORMATION: X may be Gln or Glu

<400> SEQUENCE: 2

```
Ile Pro Gly Leu His Pro Ile Leu Thr Leu Ser Lys Xaa Asp Xaa Thr
1               5                   10                  15

Leu Ala Val Tyr Xaa Xaa Ile Leu Thr Ser Xaa Pro Ser Arg Xaa Val
            20                  25                  30

Ile Xaa Ile Ser Xaa Asp Leu Glu Xaa Leu Arg Asp Leu Leu His Val
        35                  40                  45

Leu Ala Phe Ser Lys Ser Cys His Leu Pro Xaa Ala Ser Gly Leu Glu
    50                  55                  60

Thr Leu Asp Ser Leu Gly Gly Val Leu Glu Ala Ser Gly Tyr Ser Thr
65                  70                  75                  80

Glu Val Val Ala Leu Ser Arg Leu Xaa Gly Ser Leu Xaa Asp Xaa Leu
                85                  90                  95

Xaa Xaa Leu Asp Leu Ser Pro Gly Cys
            100                 105

<210> SEQ ID NO 3
<211> LENGTH: 6
<212> TYPE: PRT
<213> ORGANISM: Homo sapiens

<400> SEQUENCE: 3

Met Val Pro Ile Gln Lys
1               5

<210> SEQ ID NO 4
<211> LENGTH: 6
<212> TYPE: PRT
<213> ORGANISM: Homo sapiens

<400> SEQUENCE: 4

Val Gln Asp Asp Thr Lys
1               5

<210> SEQ ID NO 5
<211> LENGTH: 4
<212> TYPE: PRT
<213> ORGANISM: Homo sapiens

<400> SEQUENCE: 5

Thr Leu Ile Lys
1

<210> SEQ ID NO 6
<211> LENGTH: 5
<212> TYPE: PRT
<213> ORGANISM: Homo sapiens

<400> SEQUENCE: 6

Thr Ile Val Thr Arg
1               5

<210> SEQ ID NO 7
<211> LENGTH: 13
<212> TYPE: PRT
<213> ORGANISM: Homo sapiens

<400> SEQUENCE: 7

Ile Asn Asp Ile Ser His Thr Gln Ser Val Ser Ser Lys
1               5                   10

<210> SEQ ID NO 8
```

```
<211> LENGTH: 18
<212> TYPE: PRT
<213> ORGANISM: Homo sapiens

<400> SEQUENCE: 8

Val Thr Gly Leu Asp Phe Ile Pro Gly Leu His Pro Ile Leu Thr Leu
1               5                   10                  15

Ser Lys

<210> SEQ ID NO 9
<211> LENGTH: 13
<212> TYPE: PRT
<213> ORGANISM: Homo sapiens

<400> SEQUENCE: 9

Asn Val Ile Gln Ile Ser Asn Asp Leu Glu Asn Leu Arg
1               5                   10

<210> SEQ ID NO 10
<211> LENGTH: 10
<212> TYPE: PRT
<213> ORGANISM: Homo sapiens

<400> SEQUENCE: 10

Asp Leu Leu His Val Leu Ala Phe Ser Lys
1               5                   10

<210> SEQ ID NO 11
<211> LENGTH: 34
<212> TYPE: PRT
<213> ORGANISM: Homo sapiens

<400> SEQUENCE: 11

Ser Cys His Leu Pro Trp Ala Ser Gly Leu Glu Thr Leu Asp Ser Leu
1               5                   10                  15

Gly Gly Val Leu Glu Ala Ser Gly Tyr Ser Thr Glu Val Val Ala Leu
            20                  25                  30

Ser Arg

<210> SEQ ID NO 12
<211> LENGTH: 18
<212> TYPE: PRT
<213> ORGANISM: Homo sapiens

<400> SEQUENCE: 12

Leu Gln Gly Ser Leu Gln Asp Met Leu Trp Gln Leu Asp Leu Ser Pro
1               5                   10                  15

Gly Cys

<210> SEQ ID NO 13
<211> LENGTH: 18
<212> TYPE: PRT
<213> ORGANISM: Homo sapiens

<400> SEQUENCE: 13

Val Thr Gly Leu Asp Phe Ile Pro Gly Leu His Pro Ile Leu Thr Leu
1               5                   10                  15

Ser Lys
```

METHODS OF INHIBITING SEIZURE IN A SUBJECT

CROSS REFERENCE TO RELATED APPLICATIONS

This application claims priority from U.S. Provisional Application Ser. No. 60/951,793 filed on Jul. 25, 2007, which is hereby incorporated by reference in its entirety.

GOVERNMENTAL RIGHTS

This work was supported by the Juvenile Diabetes Foundation, grant number 1-2004-594, National Institutes of Health, grant numbers NS 042744, R01 NS 042936, R01 NS056872, and the Neuroscience Blueprint Core, grant number P30 NS057105. The U.S. Government has certain rights in this invention.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f).adsf

FIELD OF THE INVENTION

The invention relates to methods for the treatment of epileptic and non-epileptic seizures and associated symptoms. The invention also relates to methods for increasing leptin levels in a subject

BACKGROUND OF THE INVENTION

Epilepsy is a common chronic neurological disorder that is characterized by recurrent unprovoked seizures. These seizures are transient signs or symptoms due to abnormal, excessive or synchronous neuronal activity in the brain. About 50 million people worldwide have epilepsy at any one time. Epilepsy is usually controlled, but not cured, with medication. While medication or surgery provide seizure control in most cases, over 30% of people with epilepsy do not have seizure control even with the best available medications.

The first line of treatment for epilepsy is anticonvulsant medication. Some people with epilepsy will experience a complete remission when treated with an anticonvulsant medication. If this does not occur, the dose of medication may be increased, or another medication may be added to the first. The general strategy is to increase the medication dose until either the seizures are controlled, or until dose-limiting side effects appear; at which point the medication dose is reduced to the highest amount that does not produce undesirable side effects. If a person's epilepsy cannot be brought under control after adequate trials of two or three different medications, that person's epilepsy is generally classified as "medically refractory."

Surgical treatment can be an option for epilepsy when an underlying brain abnormality, such as a benign tumor or an area of scar tissue (e.g. hippocampal sclerosis) can be identified. The abnormality must be removable by a neurosurgeon. Surgery is usually only offered to patients when their epilepsy has not been controlled by adequate attempts with multiple medications. The most common form of resective surgical treatment for epilepsy is to remove the front part of either the right or left temporal lobe.

For those with medically refractory epilepsy that are not candidates for surgery or for whom surgery has not worked, few treatment options exist. One option is the ketogenic diet, a high-fat, low-carbohydrate, and adequate protein diet. While the ketogenic diet is effective in children with medically refractory epilepsy, its adverse effects and the parental effort involved in implementing and maintaining the diet limit its use.

Another treatment option is the use of neuropeptides that have anticonvulsant effects. Both neuropeptide Y and galanin have anticonvulsant effects in seizure animal models. However, the potential of neuropeptides as anticonvulsants remains unexploited except for adrenocorticotropic hormone, which is an accepted treatment for some childhood epilepsies. The clinical utility of neuropeptides such as neuropeptide Y and galanin is limited because they are not suited for peripheral administration since they do not cross the blood-brain barrier.

Due to the adverse effects and uncertainty associated with the few treatment options for those with medically refractory epilepsy, there is a need for new treatment options. Further, an easily administrated, highly effective anticonvulsant medication that crosses the blood-brain barrier is highly desired.

BRIEF SUMMARY OF THE INVENTION

It is an aspect of the invention to provide a method for inhibiting seizures in a subject. In one embodiment, the method comprises intranasally administering a composition comprising leptin to the subject. In another embodiment, the method comprises administering a compound that activates at least one leptin receptor in the brain of the subject. In a further embodiment, the method comprises administering a composition comprising leptin to the subject such that brain leptin levels are increased to greater than about 10, 12, 13, 14, 15, 16, 17, 18, 19, 20, 23, 25, 27, 30 pg/mg or more in the subject.

Other aspects and iterations of the invention are described more thoroughly below.

A, In 6-8 week old CD-1 mice, 800 µg/kg leptin (n=8) given intranasally (IN) 30 minutes prior to a 75 mg/kg intraperitoneal injection of pentylenetetrazole (PTZ) significantly increased the latency to behaviorally assessed generalized clonic-tonic seizures compared to mice receiving vehicle (Veh, n=11). Eight (n=6) and 80 (n=6) µg/kg IN leptin also increased PTZ seizure latency, but the differences were not statistically significant. B and C, Brain and serum leptin levels are significantly increased after 800 µg/kg IN leptin. These graphs include all animals given IN leptin (n=6 for 8 µg/kg, n=6 for 80 µg/kg and n=13 for 800 µg/kg doses) or vehicle (n=14 for Veh), including animals given PTZ presented in A. For brain leptin levels shown in B, only the 800 µg/kg dose produced significantly higher leptin levels (800 µg/kg vs. Veh and 800 µg/kg vs. 80 µg/kg are significantly different). For serum leptin levels shown in C, both 80 and 800 µg/kg doses produced significant elevation of leptin levels (800 µg/kg dose vs. Veh and 8 µg/kg dose, and 80 µg/kg dose vs. Veh are significantly different). Note the Y-Axis break in C. For A-C, statistical analysis was performed by Kreskas-Wallis test for all doses with Dunn's multiple comparison test for dose pair comparisons.

Figure 3:
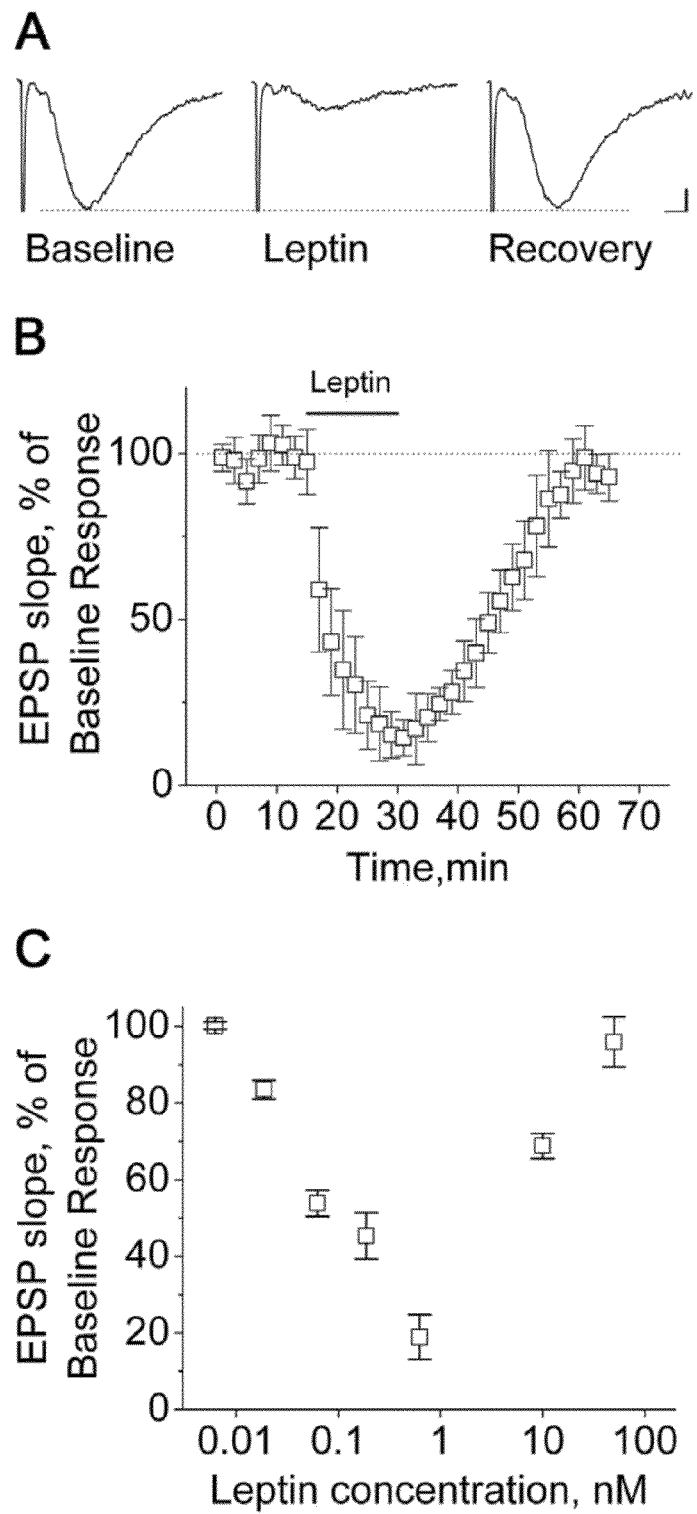

FIG. 3 depicts the inhibition of CA1 field excitatory postsynaptic potentials (fEPSPs) by leptin. A, Representative tracings of Schaffer collateral evoked fEPSPs recorded in CA1 from a mouse hippocampal slice at baseline during perfusion of ACSF (Baseline), after a 20 min perfusion with 0.6 nM leptin (Leptin), and after 30 min of washout with artificial cerebrospinal fluid (ACSF) (Recovery). Calibration 2 ms, 0.1 mV. B, Time course of fEPSP slope demonstrates inhibition of the fEPSP during a 20 min application of 0.6 nM leptin as indicated by the bar, which almost completely recovers after 30 min of washout with ACSF (n=7 slices, 6 mice). fEPSP slopes at each time point were normalized to slope of the baseline fEPSPs, which is indicated by the dotted line. Only every $3^{rd}$ point is shown for clarity. C, U-shaped concentration-response curve of leptin inhibition of fEPSP slope demonstrates maximal inhibition at 0.6 nM and minimal inhibition at 0.006 nM and 50 nM leptin (n=6 slices, 2 mice).

Figure 4:
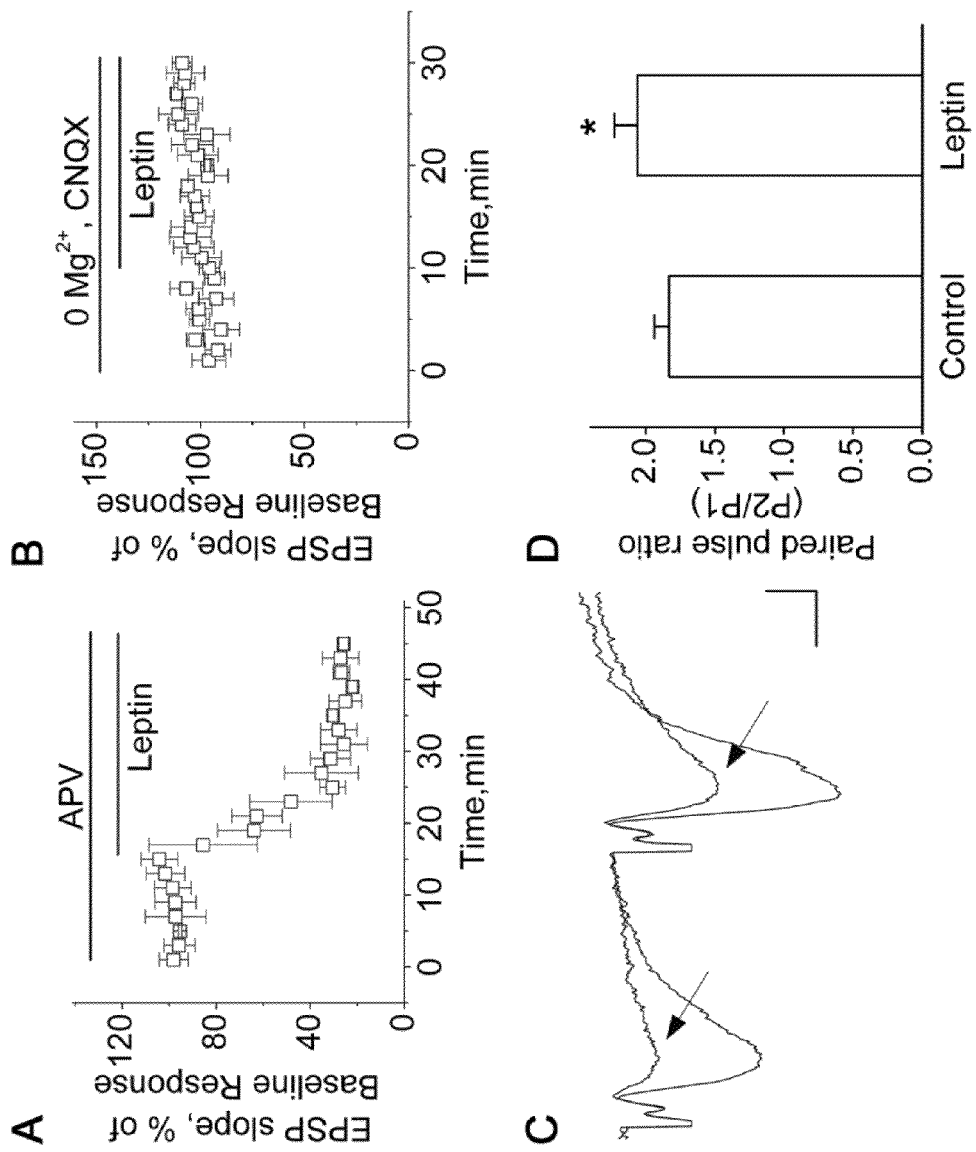

FIG. 4 depicts the selective inhibition of the α-amino-3-hydroxy-5-methyl-4-isoxazole-proprionic acid receptor (AMPAR) mediated component of the CA1 fEPSP in hippocampal slices by leptin. A, Leptin inhibited the AMPAR component of the CA1 fEPSP. Time course of the fEPSP slope for the AMPAR component after a bath applying 0.6 nM leptin as indicated by bar (n=4 slices, 2 mice). The AMPAR component was isolated by adding the NMDA antagonist D-2-amino-5-phosphonovaleric acid (D-APV) (50 µM) as indicated by bar. B, In contrast, leptin did not inhibit the N-methyl d-aspartate receptor (NMDAR) component of the CA1 fEPSP. Time course of the fEPSP slope for the NMDA component after a bath applying 0.6 nM leptin as indicated by bar (n=6 slices, 4 mice). The NMDAR component was isolated by adding the AMPAR antagonist 6-cyano-7-nitroquinoxaline-2,3-dione (CNQX) (10 µM) in $Mg^{2+}$-free ACSF. Data in A and B analyzed as in FIG. 3B. Bars indicate when $Mg^{2+}$-free ACSF and leptin were applied. C-D, Leptin enhances paired pulse facilitation. C, Superimposed representative pairs of CA1 fEPSPs from the same slice demonstrate fEPSP inhibition and increased paired pulse facilitation in 0.6 nM leptin (arrows). Interstimulus interval 25 ms, calibration 4 ms, 0.2 mV. D, Cumulative data from 5 slices (5 mice) comparing the paired pulse facilitation ratio (PPF=P2/P1 where P1 is the slope of the first fEPSP and P2 is the slope of the second fEPSP) before and after applying 0.6 nM leptin for 20 min (*p<0.02, paired t-test).

Figure 5:
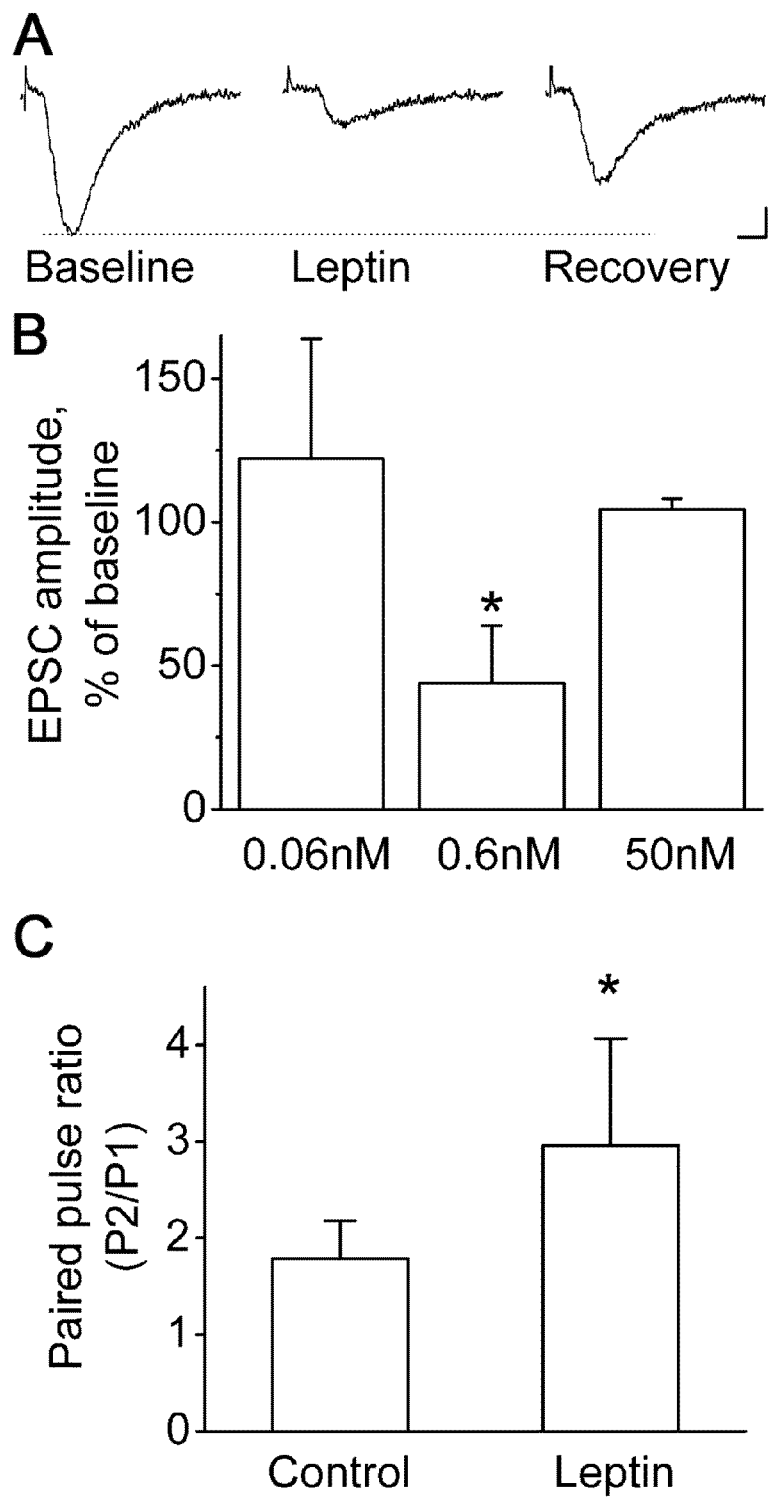

FIG. 5 depicts the leptin inhibition of AMPAR mediated excitatory postsynaptic currents (EPSCs) obtained from voltage-clamped CA1 pyramidal neurons in mouse hippocampal slices. A, Representative tracings of Schaffer collateral evoked whole-cell EPSCs recorded from a CA1 neuron voltage-clamped at −70 mV at baseline during perfusion of ACSF containing 2 mM $CaCl_2$ and 1 mM $MgCl_2$ (Baseline), after a 10 min perfusion with 0.6 nM leptin (Leptin), and after 20 min of washout with ACSF (Recovery). Calibration 5 ms, 25 pA. B, Leptin inhibited AMPAR mediated EPSCs with a U-shaped dose-response relationship. Peak amplitudes of AMPAR mediated EPSCs after a 10 min perfusion with varying leptin concentrations expressed as a percentage of the peak amplitude of the baseline EPSC (n=5-9 cells). *p<0.001 for 0.6 nM vs. 0.06 nM, and *p<0.01 for 0.6 vs. 50 nM leptin (ANOVA with Tukey-Kramer test for multiple comparisons). C, Leptin enhanced paired pulse facilitation. The paired-pulse ratio was calculated as in FIG. 4 using peak amplitudes of pairs of EPSCs evoked with an interstimulus interval of 25 ms in 0.6 nM leptin. *p<0.02 (paired t-test).

Figure 6:
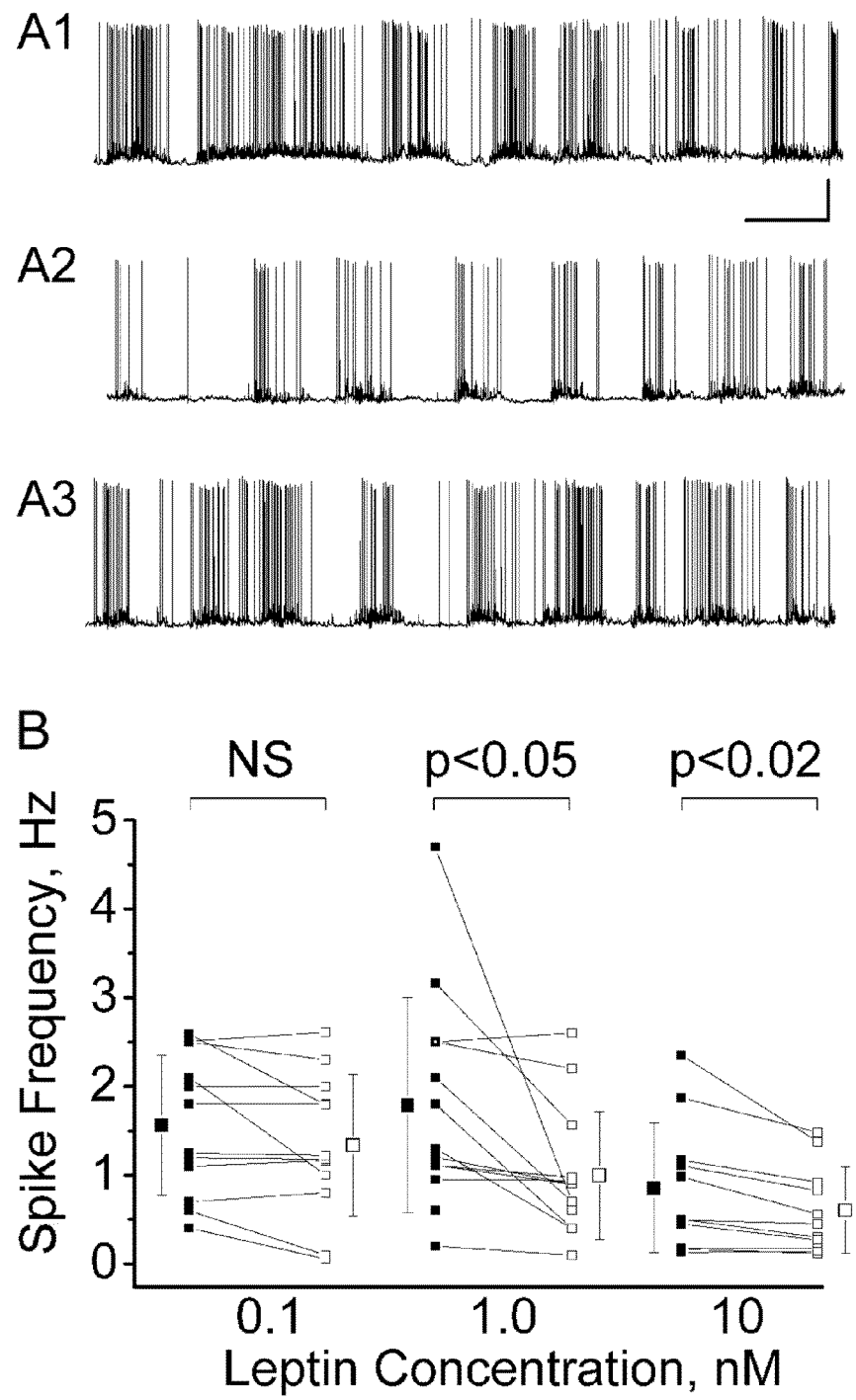

FIG. 6 depicts the leptin inhibition of low magnesium-induced spiking in cultured hippocampal neurons. A1, Whole-cell patch recordings from cultured hippocampal neurons in current clamp configuration spontaneously fire action potentials in nominally magnesium free external solution. Baseline membrane potential −57 mV. Calibration for A1-A3 is 10 s, 30 mV. A2, Leptin (1 nM) reduces action potential firing frequency by 30-40%. A3, Action potential firing recovers close to baseline frequency after leptin wash out. B, Cumulative data comparing spike frequency in low magnesium before (filled squares) and after (open squares) application of different leptin concentrations. Each filled and open symbol connected by a line represents one cell, and its firing frequency before and after leptin. Therefore, each line represents one matched data pair; some data points are superimposed on each other. The average plus SD are presented beside each data set with a larger symbol. Significant reduction in spike frequency is produced by 1 nM (n=13 cells) and 10 nM (n=11 cells), but not 0.01 nM (n=12 cells) leptin (paired t-test).

Figure 7:
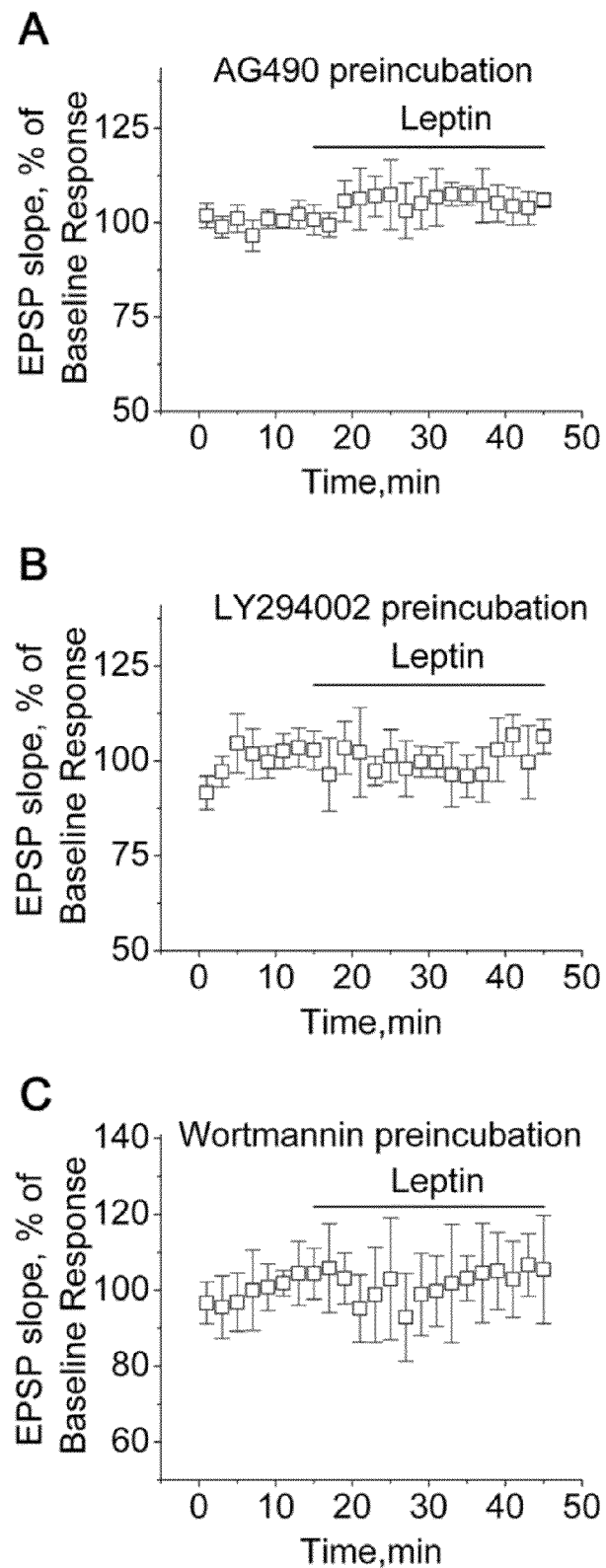

FIG. 7 depicts the leptin inhibition of CA1 fEPSPs dependency on Janus tyrosine kinase 2 (JAK2) and phosphoinositide 3-kinase (PI3K) activation. The JAK2 inhibitor AG490 and the PI3K inhibitors LY294002 and wortmannin prevent leptin-induced fEPSP inhibition. Time course of CA1 fEPSP slopes after applying 0.6 nM leptin as indicated by the bar in slices pretreated for at least 3 hours in A, 20 µM AG-490 (n=5 slices, 3 mice), B, 16 µM LY294002 (n=7 slices, 2 mice), or C, 50 nM wortmannin (n=6 slices, 2 mice). Data analyzed as in FIG. 3B.

Figure 8:
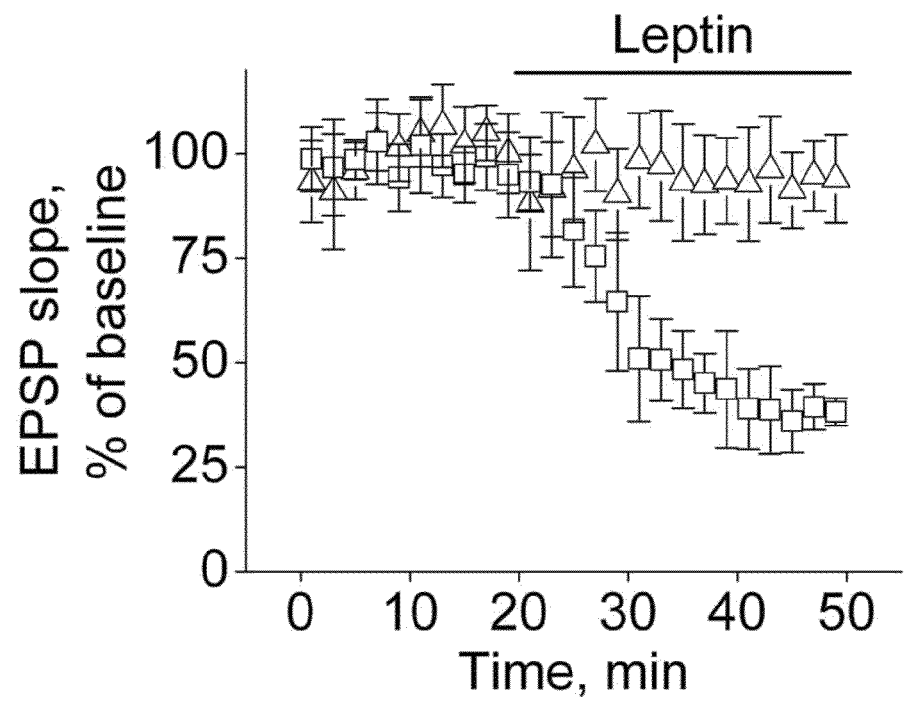

FIG. 8 depicts the leptin inhibition of CA1 fEPSPs dependency on the long form of the leptin receptor. Leptin did not inhibit fEPSPs in hippocampal slices obtained from leptin receptor (Ob-Rb) deficient db/db mice, but did inhibit fEPSPs in slices from wild-type C57BLKS/J mice. Time course of CA1 fEPSPs after applying 0.6 nM leptin as indicated by the bar to slices from db/db mice (n=6 slices, 3 mice) (triangles) and C57BLKS/J mice (n=10 slices, 3 mice) (squares). Data analyzed as in FIG. 3B.

FIG. 9 depicts a time course as well as serum and brain levels of leptin after intranasal administration in two strains of mice. Intranasal administration of leptin (800 µg/kg body weight) to leptin-deficient (ob/ob) mice shows elevated leptin in both A, serum and B, brain as early as 2 minutes and as late as 30 minutes after administration. C, Leptin receptor deficient mice (db/db) have high levels of serum leptin relative to control mice (C57). Intranasal administration of leptin raises serum leptin levels slightly (db/db+lep). D, Despite high serum levels, brain leptin in leptin receptor deficient mice (db/db) remains low. Intranasal administration of leptin to leptin receptor deficient mice increases brain leptin (db/db+ lep).

FIG. 10 depicts an amino acid sequence (SEQ ID NO. 1), wherein: Xaa at position 6 may be Trp or Gln; Xaa at position 36 may be Gln or Glu; Xaa at position 40 may be Gln or Glu; Xaa at position 42 may be Ile, Leu, Met or methionine sulfoxide; Xaa at position 44 may be Trp or Gln; and Xaa at position 45 may be Gln or Glu. In a preferred embodiment, Xaa at position 6 may be Trp; Xaa at position 36 may be Gln; Xaa at position 40 may be Gln; Xaa at position 42 may be Met; Xaa at position 44 may be Trp; and Xaa at position 45 may be Gln.

FIG. 11 depicts an amino acid sequence (SEQ ID NO. 2), wherein: Xaa at position 13 may be Ile, Leu, Met or methionine sulfoxide; Xaa at position 15 may be Gln or Glu; Xaa at position 21 may be Gln or Glu; Xaa at position 22 may be Gln or Glu; Xaa at position 27 may be Ile, Leu, Met or methionine sulfoxide; Xaa at position 31 may be Asn, Asp or Gln; Xaa at position 34 may be Gln or Glu; Xaa at position 37 may be Asn, Asp or Gln; Xaa at position 41 may be Asn, Asp or Gln; Xaa at position 59 may be Trp or Gln; Xaa at position 89 may be Gln or Glu; Xaa at position 93 may be Gln or Glu; Xaa at position 95 may be Ile, Leu, Met or methionine sulfoxide; Xaa at position 97 may be Trp or Gln; and Xaa at position 98 may be Gln or Glu. In a preferred embodiment, Xaa at position 13 may be Met; Xaa at position 15 may be Gln; Xaa at position 21 may be Gln; Xaa at position 22 may be Gln; Xaa at position 27 may be Met; Xaa at position 31 may be Asn; Xaa at position 34 may be Gln; Xaa at position 37 may be Asn; Xaa at position 41 may be Asn; Xaa at position 59 may be Trp; Xaa at position 89 may be Gln; Xaa at position 93 may be Gln; Xaa at position 95 may be Met; Xaa at position 97 may be Trp; and Xaa at position 98 may be Gln.

FIG. 12 depicts a time course of leptin serum and brain levels following a 0.2 mg/kg intranasal dose in normal mice. A, Intranasal administration of leptin to normal mice shows elevated leptin levels in the brain as early as 30 seconds (Table 2), which decreased overtime, but remained elevated above baseline levels 5, 10, 30, and 120 minutes after administration. B, Serum leptin levels, detected by arterial sampling, increased as early as 90 seconds (Table 3), and continued to increase up to 2.5 minutes. The increase in serum leptin levels remained elevated over 3.5, 5, 10, 20, and 30 minutes. C, Serum leptin levels, obtained from tail vein blood (a slower process), increased until about 20 minutes, at which time the leptin levels decreased, but remained elevated at 120 minutes. D, After brain leptin levels spiked (~30 seconds, filled squares), the increase in leptin levels were detected in the serum (open squares, obtained from tail vein).

DETAILED DESCRIPTION OF THE INVENTION

The present invention provides methods of inhibiting seizures in a subject by administering to the subject a compound that activates the leptin receptor. Advantageously, the present invention provides methods of increasing the concentration in the brain of a compound that activates the leptin receptor. In particular, the present invention provides methods of administering to a subject a compound that activates the leptin receptor so that therapeutically effective amounts of the compound may be achieved in the brain of the subject. In an exemplary embodiment, a compound that activates the leptin receptor may be administered intranasally. The present invention provides methods of inhibiting seizures that are convenient. Subjects who may benefit from this invention are those suffering from seizures, including those suffering from epilepsy.

I. Compounds that Activate the Leptin Receptor

As used herein, "a compound that activates the leptin receptor," refers to a compound that binds to and activates the leptin receptor such that the JAK/STAT and/or P13 kinase signaling pathways are activated. As such, "leptin receptor," as used herein, refers to a form of the leptin receptor that, once activated, can then activate the JAK/STAT and/or P13 kinase signaling pathways (for instance, the long form of the leptin receptor). Non-limiting examples of compounds that activate the leptin receptor are human leptin and leptin of non-human mammalian species including mouse. Methods of monitoring the JAK/STAT and/or P13 kinase signaling pathways for activation are well known in the art.

(a) Leptin and Leptin Polypeptides

In some embodiments, a compound that activates the leptin receptor is leptin. Leptin is the protein product of the obese gene (ob), and may be found in several different mammalian species, including mice, humans, pigs, and cattle. Human endogenous leptin, in its mature form, is a 146-amino acid protein (See GenBank Accession number BAA09787).

In other embodiments, a variant of a leptin polypeptide may bind to and activate the leptin receptor. By way of example, such variants may include leptin polypeptides with conservative amino acid substitutions, whereby amino acids are substituted with alternative amino acids of similar stereochemistry, i.e., charge or hydrophobicity. In additional embodiments, the leptin polypeptide may be a variant resulting from alternative post-translational modification, including glycosylation, acylation, methylation, phosphorylation, sulfation, or proteolytic cleavage. In alternative embodiments, the leptin polypeptide may be a polypeptide with amino acid sequences which are about 95%, 90%, 85%, 80%, 75%, or about 70% identical to the human leptin sequence, as calculated by algorithms known in the art, for example BLAST, FASTA, or Smith-Waterman. In each of the above embodiments, the leptin polypeptide is capable of binding to and activating the leptin receptor, such that the JAK/STAT and/or P13 kinase signaling pathways are activated.

A number of leptin polypeptides that bind and activate the leptin receptor have been identified. Non-limiting examples of leptin polypeptides include SEQ ID NO. 1 (FIG. 10), as described in U.S. Pat. No. 5,521,283 (hereby incorporated by reference) and SEQ ID NO. 2 (FIG. 11), as described in U.S. Pat. No. 5,532,336, (hereby incorporated by reference). Other examples include fragments of leptin, comprising (numbered in reference to the human sequence) ob21-26 (MVPIQK) (SEQ ID NO:3), ob27-32 (VQDDTK) (SEQ ID NO:4), ob33-36 (TLIK) (SEQ ID NO:5), ob37-41 (TIVTR) (SEQ ID NO:6), ob42-54 (INDISHTQSVSSK) (SEQ ID NO:7), ob55-56 (QK), ob57-74 (VTGLDFIPGLHPILTLSK) (SEQ ID NO:8), ob93-105 (NVIQISNDLENLR) (SEQ ID NO:9), ob106-115 (DLLHVLAFSK) (SEQ ID NO:10), ob116-149 (SCHLPWASGLETLDSLGGVLEASGYSTEVVALSR) (SEQ ID NO:11), ob150-167 (LQGSLQDMLWQLDLSPGC) (SEQ ID NO:12), and ob57-74 (VTGLDFIPGLHPILTLSK) (SEQ ID NO:13) as described in PCT Patent Application WO97/46585 (hereby incorporated by reference). In addition, leptin polypeptides may comprise fragments of the leptin polypeptides above; or a polypeptide comprising any one or more of the polypeptides above (especially contiguous polypeptides); or a functional derivative, analogue or variant thereof. Suitable leptin polypeptides comprise at least 4 amino acids. The leptin polypeptides of the invention may be prepared using conventional digestion methods, synthetic techniques or by use of standard expression methodology.

Leptin polypeptides may also comprise amino acid residues 21-35, 31-45, 41-55, 51-65, and 116-122 of native human leptin as described in U.S. Pat. No. 6,777,388 (hereby incorporated by reference). Alternatively, leptin polypeptides may comprise amino acids 57-92, 22-56, and 116-177 of mouse or human leptin, preferably human leptin, as described by Samson et al. Endocrinology 1996, 137(11): 5182-5185 (hereby incorporated by reference). In another alternative, leptin polypeptides may comprise amino acids residues 116-130 of mouse leptin, as disclosed by Rozhavskaya-Arena et al., in Endocrinology, Vol. 141(7) (hereby incorporated by reference). Leptin polypeptides may also contain D-amino acids as disclosed in U.S. Pat. No. 7,208,572 (hereby incorporated by reference).

Compounds that activate the leptin receptor may also encompass functional derivatives of leptin polypeptides, including salts and solvates of the polypeptides mentioned herein. Additionally, the leptin polypeptides may be chemically modified by the attachment of groups or moieties so as to improve the physical properties, such as stability, or the therapeutic properties, for example the pharmacokinetic properties, of the polypeptide.

(b) Other Compounds that Activate the Leptin Receptor

It will be appreciated that the invention includes both polypeptide and non-polypeptide compounds that activate the leptin receptor. In some embodiments, a compound that activates the leptin receptor is a non-polypeptide agonist or a small molecule agonist. Such compounds may be prepared and tested according to known procedures, for example, see those disclosed in GB2292382.

In certain embodiments, a compound that activates a leptin receptor may be an antibody. Typically, the antibody would bind to and activate the leptin receptor such that the JAK/STAT and/or P13 kinase signaling pathways are activated.

(c) Pharmaceutical Dosage Form

Compounds that activate the leptin receptor may be formulated into pharmaceutical compositions and administered by a number of different means that will deliver a therapeutically effective dose. Such compositions may be administered, by way of example, enterally, including orally or gastricly (i.e. a feeding tube). A compound may also be administered parenterally, including subcutaneously, intravenously, intramuscularly, or by intrathecal injection or infusion techniques. Additionally, a compound may be administered topically, including intradermally or transdermally. Topical administration may involve the use of transdermal patches or iontophoresis devices. Also included is transmucosal administration including intranasal absorption through the mucous membrane by inhalation spray or insufflation. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Regardless of the route of administration, compounds that activate the leptin receptor may be in the form of free bases or pharmaceutically acceptable salts thereof. Pharmaceutically acceptable salts may include pharmaceutically acceptable acid addition salts. Acid addition salts of the compounds may be prepared in a standard manner in a suitable solvent from the parent compound and an excess of an acid such as hydrochloric, hydrobromic, hydroiodic, nitric, carbonic, sulphuric, phosphoric, acetic, maleic, succinic, or methanesulphonic. Certain compounds form inner salts or zwitterions that may be acceptable. Cationic salts are prepared by treating the parent compound with an excess of an alkaline reagent, such as a hydroxide, carbonate or alkoxide containing the appropriate cation. Cations such as $Na^+$, $K^+$, $Ca^{2+}$, and $NH_4^+$ are examples of cations present in pharmaceutically acceptable salts. Solvates include pharmaceutically acceptable solvates, such as hydrates.

Suitable pharmaceutically acceptable acid addition salts of compounds may be prepared from organic acids. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid.

Suitable pharmaceutically-acceptable base addition salts of compounds of use in the present methods include metallic salts made from aluminum, calcium, lithium, magnesium, potassium, sodium and zinc or organic salts made from N, N'-dibenzylethylenediamine, chloroprocaine, choline, diethanolamine, ethylenediamine, meglumine-(N-methylglucamine) and procaine. All of these salts may be prepared by conventional means from the corresponding compound by reacting, for example, the appropriate acid or base with the compounds of the invention.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols may be used. Mixtures of solvents and wetting agents such as those discussed above are also useful.

Solid dosage forms for oral administration may include capsules, tablets, pills, powders, and granules. In such solid dosage forms, the compound is ordinarily combined with one or more adjuvants appropriate to the indicated route of administration. If administered per os, the compound may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation, for example, a dispersion of active compound in hydroxypropylmethyl cellulose. In the case of capsules, tablets, and pills, the dosage forms may also comprise buffering agents such as sodium citrate, or magnesium or calcium carbonate or bicarbonate. Tablets and pills can additionally be prepared with enteric coatings. For oral administration, a pharmaceutically acceptable nontoxic composition is formed by incorporating any of the normally employed excipients, such as those carriers previously listed, and generally about 10% to about 95% of one or more compounds of the invention. More preferably, a composition may comprise about 25% to about 75% of one or more compounds of the invention.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

For intrathecal administration, pharmaceutical compositions of the invention may be delivered in an appropriate vehicle such as saline, by a single injection or as a continuous infusion with the use of a pump, (e.g. an osmotic minipump).

For aerosol administration, compounds that activate the leptin receptor may be supplied in a finely divided form along with an aerosol surfactant and propellant. Typical percentages of compounds that activate the leptin receptor in a composition for aerosol administration may be between about 0.01% to about 40% by weight, preferably about 1% to about 10% by weight. The aerosol surfactant is typically nontoxic, and preferably suitable to the propellant. Such agents may include the esters or partial esters of fatty acids containing from 6 to 22 carbon atoms such as caproic, octanoic, lauric, palmatic, stearic linoleic, linolenic, olesteric and oleic acids with an aliphatic polyhydric alcohol or its cyclic anhydride. Mixed esters, such as mixed or natural glycerides may also be utilized. The aerosol surfactant may typically constitute about 0.1% to about 20% by weight of the composition, preferably about 0.25% to about 5%. The balance of the composition is ordinarily propellant. A carrier can also be included, as desired, as with, e.g., lecithin for intranasal delivery.

Compounds that activate the leptin receptor may also be administered intranasally. Intranasal administration may be via a powder or solution, by way of example, a finely divided form, a mist, or an aerosol. As a powder, a compound that activates the leptin receptor may, by way of example, comprise a lyophilized powder and may further comprise any carriers or excipients described above. A compound that activates the leptin receptor may be formulated as a solution, optionally isotonic relative to nasal secretions and of about the same pH, ranging from: about pH 4 to about pH 4.5, about pH 4.5 to about pH 5, about pH 5 to about pH 5.5, about pH 5.5 to about pH 6, about pH 6 to about pH 6.5, about pH 6.5 to about pH 7, about pH 7 to about pH 7.5, about pH 7.5 to about pH 8, preferably from about pH 4 to about pH 6, or about pH 6.0 to about pH 7.4. Buffers should be physiologically compatible including, by way of example, phosphate buffers.

Compounds that activate the leptin receptor may be formulated with one or more mucosal delivery-enhancing agents wherein absorption or dosage release is optimized or sustained for an effective delivery period. An effective delivery period may be by way of non-limiting example: from less that 0.01 hours to about 24 hours; about 0.01 to about 0.1 hours; about 0.1 to 0.5 hours; about 0.5 to about 1 hour; about 1 hour to about 1.5 hours; about 1.5 to about 2 hours; about 2 to about 5 hours; about 5 to about 7 hours; about 7 to about 10 hours; about 10 to about 12 hours; about 12 to about 24 hours; or more that 24 hours; preferably about 0.1 to about 0.5 hours following mucosal administration. The sustained release of a compound that activates the leptin receptor may be facilitated by repeated administration.

In one embodiment the present invention provides mucosal (e.g., nasal) delivery of a formulation comprising a compound that activates the leptin receptor in combination with one or more mucosal delivery-enhancing agents and an optional sustained release-enhancing agent or agents. Mucosal delivery-enhancing agents yield an effective increase in delivery of therapeutic active agent. Another factor affecting therapeutic activity of a compound that activates the leptin receptor in the blood plasma and CNS is residence time (RT). Sustained release-enhancing agents, in combination with intranasal delivery-enhancing agents, increase the effective concentration and increase residence time (RT) of leptin or compounds that activate the leptin receptor. Polymeric delivery vehicles and other agents and methods yielding sustained release-enhancing formulations, for example, polyethylene glycol (PEG), are disclosed in U.S. Pat. No. 7,186,691 which is incorporated herein by reference.

A compound that activates the leptin receptor may be combined or coordinately administered with a suitable carrier or vehicle for mucosal delivery. As used herein, the term "carrier" means a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories can be found in the U.S. Pharmacopeia National Formulary, 1857 1859, (1990). Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other non toxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like. The amount of active ingredient that can be combined with the carrier materials to produce a single dosage form will vary depending upon the particular mode of administration.

As used herein, "mucosal delivery-enhancing agents" include agents which enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery, or at a selected target site of activity such as the bloodstream or central nervous system) of leptin or compounds that activate the leptin receptor. Enhancement of mucosal delivery can thus occur by any of a variety of mechanisms, for example by increasing the diffusion, transport, persistence or stability of leptin or compounds that activate the leptin receptor, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, and other mechanisms.

Within certain aspects of the invention, absorption-promoting agents for coordinate administration or combinatorial formulation with leptin or compounds that activate the leptin receptor are selected from small hydrophilic molecules, including but not limited to, dimethyl sulfoxide (DMSO), dimethylformamide, ethanol, propylene glycol, and the 2-pyrrolidones. Alternatively, long-chain amphipathic molecules, for example, deacylmethyl sulfoxide, azone, sodium laurylsulfate, oleic acid, and the bile salts, may be employed to enhance mucosal penetration of the leptin or compounds that activate the leptin receptor. In additional aspects, surfactants (e.g., polysorbates) are employed as adjunct compounds, processing agents, or formulation additives to enhance intranasal delivery of the leptin receptor-binding peptide. Agents such as DMSO, polyethylene glycol, and ethanol can, if present in sufficiently high concentrations in delivery environment (e.g., by pre-administration or incorporation in a therapeutic formulation), enter the aqueous phase of the mucosa and alter its solubilizing properties, thereby enhancing the partitioning of a compound that activates the leptin receptor from the vehicle into the mucosa.

Additional mucosal delivery-enhancing agents that may be useful include, but are not limited to, mixed micelles; enamines; nitric oxide donors (e.g., S-nitroso-N-acetyl-DL-penicillamine, NOR1, NOR4, which are preferably co-administered with an NO scavenger such as carboxy-PITO or doclofenac sodium); sodium salicylate; glycerol esters of acetoacetic acid (e.g., glyceryl-1,3-diacetoacetate or 1,2-isopropylideneglycerine-3-acetoacetate); and other release-diffusion or intra- or trans-epithelial penetration-promoting agents that are physiologically compatible for mucosal delivery. Other absorption-promoting agents are selected from a variety of carriers, bases and excipients that enhance mucosal delivery, stability, activity or trans-epithelial penetration of a compound that activates the leptin receptor. These include, inter alia, cyclodextrins and β-cyclodextrin derivatives (e.g., 2-hydroxypropyl-β-cyclodextrin and heptakis(2,6-di-O-methyl-β-cyclodextrin). These compounds, optionally conjugated with one or more of the active ingredients and further optionally formulated in an oleaginous base, enhance bioavailability in the mucosal formulations of the invention. Yet additional absorption-enhancing agents adapted for mucosal delivery include medium-chain fatty acids, including mono- and diglycerides (e.g., sodium caprate extracts of coconut oil, Capmul), and triglycerides (e.g., amylodextrin, Estaram 299, Miglyol 810).

The mucosal therapeutic and prophylactic compositions of the present invention may be supplemented with any suitable penetration-promoting agent that facilitates absorption, diffusion, or penetration of leptin or compounds that activate the leptin receptor across mucosal barriers. The penetration promoter may be a promoter that is pharmaceutically acceptable. Thus, in more detailed aspects of the invention compositions are provided that incorporate one or more penetration-promoting agents selected from sodium salicylate and salicylic acid derivatives (acetyl salicylate, choline salicylate, salicylamide, etc.); amino acids and salts thereof (e.g. monoaminocarboxlic acids such as glycine, alanine, phenylalanine, proline, hydroxyproline, etc.; hydroxyamino acids such as serine; acidic amino acids such as aspartic acid, glutamic acid, etc; and basic amino acids such as lysine arginine and histidine, inclusive of their alkali metal or alkaline earth metal salts); and N-acetylamino acids (N-acetylalanine, N-acetylphenylalanine, N-acetylserine, N-acetylglycine, N-acetyllysine, N-acetylglutamic acid, N-acetylproline, N-acetylhydroxyproline, etc.) and their salts (alkali metal salts and alkaline earth metal salts). Also provided as penetration-promoting agents within the methods and compositions of the invention are substances which are generally used as emulsifiers (e.g. sodium oleyl phosphate, sodium lauryl phosphate, sodium lauryl sulfate, sodium myristyl sulfate, polyoxyethylene alkyl ethers, polyoxyethylene alkyl esters, etc.), caproic acid, lactic acid, malic acid and citric acid and alkali metal salts thereof, pyrrolidonecarboxylic acids, alkylpyrrolidonecarboxylic acid esters, N-alkylpyrrolidones, proline acyl esters, and the like. Also employed may be permeation enhancers including but not limited to sodium taurodihydrofisidiate (STDHF), and or lysophosphatidylcholine at a concentration of about 0.1% to about 0.5%, about 0.5% to about 1%, from about 1% to about 5%, or preferably about 1%.

A therapeutically effective amount of a compound that activates the leptin receptor that may be combined with the carrier materials to produce a single dosage of the composition will vary depending upon the patient and the particular mode of administration. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix 11, pp. 475-493.

(d) Nucleic Acids Encoding Compounds that Activate the Leptin Receptor

In one embodiment of the present invention, nucleic acids that encode compounds that activate the leptin receptor may be administered to inhibit seizure. Once the coding sequence of one or more compounds that activate the leptin receptor has been obtained, it may be operably linked to suitable control elements to provide an expressible nucleic acid molecule using standard cloning or molecular biology techniques. See, e.g., Edge (1981) Nature 292:756; Nambair et al. (1984) Science 223:1299; and Jay et al. (1984) J. Biol. Chem. 259: 6311. The nucleic acid molecule may then be used per se or may be inserted into a suitable expression vector such as a plasmid or viral vector construct. Expression vectors that may be effective for the expression of compounds that activate the leptin receptor include, but are not limited to, the PcDNA 3.1, EPITAG, PRCCMV2, PREP, PVAX, PCR2-TOPOTA vectors (Invitrogen, Carlsbad Calif.), PCMV-SCRIPT, PCMV-TAG, PEGSHIPERV (Stratagene, La Jolla Calif.), and PTET-OFF, PTET-ON, PTRE2, PTRE2-LUC, PTK-HYG (Clontech, Palo Alto Calif.). Compounds that activate the leptin receptor may be expressed using (i) a constitutively active promoter, (e.g., from cytomegalovirus (CMV), Rous sarcoma virus (RSV), SV40 virus, thymidine kinase (TK), or P.beta.actin genes), (ii) an inducible promoter (e.g., the tetracycline-regulated promoter (Gossen, M. and H. Bujard (1992) Proc. Natl. Acad. Sci. USA 89:5547-5551; Gossen, M. et al. (1995) Science 268:1766-1769; Rossi, F. M. V. and H. M. Blau (1998) Curr. Opin. Biotechnol. 9:451-456), commercially available in the T-REX plasmid (Invitrogen)); the ecdysone-inducible promoter (available in the plasmids PVGRR and PIND; Invitrogen); the FK506/rapanmycin inducible promoter; or the RU486/mifepristone inducible promoter (Rossi, F. M. V. and Blau, H. M. supra)), or (iii) a tissue-specific promoter or the native promoter of the endogenous gene encoding leptin from a normal individual.

Once constructed, the nucleic acid molecules may be administered using standard gene delivery protocols. Methods for gene delivery are known in the art, including but not limited to methods based on naked nucleic acids, liposomes, cells, retrovirus including lentiviruses, adenovirus and parvoviruses including adeno-associated virus herpes simplex virus. See, e.g., U.S. Pat. Nos. 5,589,466, 6,936,272, 5,399,346, 6,818,209, 7,232,899, and 6,106,826 which are hereby incorporated by reference. Other gene delivery mechanisms include liposome-derived systems, artificial viral envelopes, and other systems known in the art (See, e.g., Rossi, J. J. (1995) Br. Med. Bull. 51(1):217-225; Boado, R. J. et al. (1998) J. Pharm. Sci. 87(11):1308-1315; and Morris, M. C. et al. (1997) Nucleic Acids Res. 25(14):2730-2736.)

In an exemplary embodiment, a herpes-based gene delivery system is used to deliver nucleic acids encoding compounds that activate the leptin receptor to target cells. The use of herpes simplex virus (HSV)-based vectors may be especially valuable for introducing nucleic acids encoding compounds that activate the leptin receptor to cells of the central nervous system, for which HSV has a tropism. The construction and packaging of herpes-based vectors are well known to those with ordinary skill in the art. A replication-competent herpes simplex virus (HSV) type 1-based vector has been used to deliver a reporter gene to the eyes of primates (Liu, X. et al. (1999) Exp. Eye Res. 169:385-395). The construction of a HSV-1 virus vector has also been disclosed in detail in U.S. Pat. No. 5,804,413 to DeLuca ("Herpes simplex virus strains for gene transfer"), which is hereby incorporated by reference. U.S. Pat. No. 5,804,413 teaches the use of recombinant HSV d92 that consists of a genome containing at least one exogenous gene to be transferred to a cell under the control of the appropriate promoter. Also taught by this patent are the construction and use of recombinant HSV strains deleted for ICP4, ICP27 and ICP22. For HSV vectors, see also Goins, W. F. et al. (1999) J. Virol. 73:519-532 and Xu, H. et al. (1994) Dev. Biol. 163:152-161, hereby incorporated by reference. The manipulation of cloned herpesvirus sequences, the generation of recombinant virus following the transfection of multiple plasmids containing different segments of the large herpesvirus genomes, the growth and propagation of herpesvirus, and the infection of cells with herpesvirus are techniques well known to those of ordinary skill in the art.

The various nucleic acids and their delivery systems described in this section may be prepared in a variety of formulations and administered through a variety of different routes, as described above in section IC. Preferably, nucleic acids encoding compounds that activate the leptin receptor may be packaged in a HSV delivery system and a therapeutically effective amount administered intranasally via an aerosol.

(e) Devices for Administration

As described above, intranasal administration of a compound that activates the leptin receptor may be by way of solution, aerosol, or a solid or powdered form. The agent may be administered by insufflation or nasal aspiration directly from any suitable platform or container. Optionally a device may be used to facilitate administration of the agent to a subject. Devices to deliver intranasal medications are known in the art. A non-limiting example of a device used to deliver a powder is disclosed in WO/1999/019330. A device may be comprised of a simple channel to direct the agent to the nasal passage. Alternatively, devices may be designed to measure and control various parameters of administration such as dosage, atomization partial size, and/or mixing with other therapeutics, mucosal permeating agents, or excipients. Compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use for intranasal delivery or as an inhaler or insufflator can be formulated containing a powder mix of the compound and a suitable powder base, for example, lactose, or starch. Alternatively devices may be designed to manually expel leptin or compounds that activate the leptin receptor. For example, a simple compressible bottle that the user may insert nasally and squeeze whereby the agent is expelled drop wise or by means of air pressure may provide a simple and convenient form of intranasal administration.

(f) Combinations of Compounds that Activate the Leptin Receptor

In certain embodiments, more than one compound that activates the leptin receptor may be administered to a subject. Such compounds may be administered to the subject simultaneously or sequentially. Alternatively, a compound that activates the leptin receptor may be administered to a subject in conjunction with a second compound known in the art to inhibit seizures.

II. Inhibition of Seizure

One aspect of the invention encompasses methods for inhibiting seizures in a subject. In certain embodiments, the method comprises administering to the subject a compound that activates the leptin receptor in the brain of the subject. In an exemplary embodiment, the compound is administered intranasally.

(a) Types of Seizure

Compounds that activate the leptin receptor may be administered to inhibit seizures regardless of origin, including seizures which have not been categorized, or which have been categorized as symptomatic, idiopathic, generalized, or partial. By way of non-limiting example, partial seizures include: seizures of the temporal lobe, such as epileptic seizures of the amygdalo-hippocampal (mesiobasal limbic or rhinencephalic) of which hippocampus seizures are a common form; lateral temporal seizures, including simple seizures that may progress into complex partial seizures; frontal lobe epileptic seizures, including supplementary motor seizures, cingulated seizures, anterior frontopolor region seizures, orbitofrontal seizures, dorsolateral seizures, opercular seizures, and motor cortex seizures. Also included are seizures derived from parietal lobe epilepsies and occipital lobe epilepsies.

By way of non-limiting example, generalized seizures include, benign neonatal familial convulsions, benign neonatal convulsions, benign myoclonic epilepsy, childhood absence epilepsy, juvenile absence epilepsy, juvenile myoclonic epilepsy, epilepsy with generalized tonic clonic seizures on awakening; infantile spasms, Lennox-Gastaut syndrome, epilepsy with myoclonic-astaric seizures, epilepsy with myoclonic absences symptomatic, febrile seizures and other generalized epilepicies and syndromes.

Idiopathic epilepsies are divided into partial and generalized sub-types. Partial (focal or local) epileptic fits arise from localized cortical discharges, such that only certain groups of muscles are involved and consciousness may be retained (Sutton, 1990). However, in generalized epilepsy, EEG discharge shows no focus such that all subcortical regions of the brain are involved. Idiopathic seizures include Idiopathic generalized epilepsies (IGE) that are the most common group of inherited human epilepsies. Included within IGE are two broad categories: the classical idiopathic generalized epilepsies (Commission on Classification and Terminology of the International League Against Epilepsy, 1989) and the newly recognized genetic syndrome of generalized epilepsy with febrile seizures plus (GEFS+) (Scheffer and Berkovic, 1997; Singh et al. 1999). The classical IGEs include a number of clinically recognizable but overlapping sub-syndromes including childhood absence epilepsy (CAE), juvenile absence epilepsy, and juvenile myoclonic epilepsy etc (Commission on Classification and Terminology of the International League Against Epilepsy, 1989; Roger et al. 1992). The sub-syndromes are identified by age of onset and the pattern of seizure types (absence, myoclonus and tonic-clonic). Also included are patients with tonic-clonic seizures alone that do not fit a specifically recognized sub-syndrome.

Also included are convulsive and non-convulsive status epilepticus. The term status epilepticus as used herein refers to any type of continuing seizure. Status epilepticus may be defined as 30 minutes or more of continuous seizure activity or a series of seizures without return to full consciousness between the seizures.

Also included are remote symptomatic seizures. The term remote symptomatic seizure as used herein refers to seizures that appear to have no acute precipitating event; however, the brain is prone to spontaneous seizures due to a prior insult or abnormality. Established causes of remote symptomatic seizures include brain malformations, stroke, intracranial infection, head trauma, meningitis, encephalitis, or neurodegenerative diseases.

(b) Inhibition of Seizure

Inhibition of seizure, for the purposes of this invention, may comprise one or more of: increased latency between a subclinical condition prior to seizure and the onset of seizure; increased latency between seizures; decreased duration of seizure; or decreased intensity of seizure which may also include a more limited or focal seizure where a generalized seizure may have occurred. Inhibition of a seizure may also include a reduction of continued epileptiform discharge.

Seizure, for the purpose of this invention, includes convulsive seizures and non-convulsive seizures. Convulsive seizure includes a sudden onset of convulsions including epileptic convulsions. Convulsions are violent spasms or a series of spasms where an individual experiences involuntary jerking, or sudden contractions of one or more muscles. Epilepsy is generally defined as a condition where an individual experiences recurrent unprovoked seizures. For the purpose of this invention non-convulsive seizure includes the condition where the subject has no convulsion, but continued epileptiform discharge may be indicated by electroencephalogram.

(c) Therapeutic Effective Amounts

Compositions containing compounds that activate the leptin receptor are typically administered to a subject in an amount sufficient to inhibit seizures in the subject. This amount is defined as a "therapeutically effective amount." The therapeutically effective amount will be determined by the efficacy or potency of the particular compound that activates the leptin receptor, the duration or frequency of administration, and the size and condition of the subject, including that subject's particular treatment response. Additionally, the route of administration should be considered when determining the therapeutically effective amount. It is anticipated that the therapeutically effective amount, in the brain, of a compound that activates the leptin receptor, may range from about 5 pg/mg total brain protein to about 500 pg/mg total brain protein. In certain embodiments, a compound that activates the leptin receptor may range from about 5 pg/ml total brain protein to about 10 pg/mg total brain protein, from about 10 pg/mg total brain protein to about 15 pg/mg total brain protein, from about 15 pg/mg total brain protein to about 20 pg/mg total brain protein, from about 20 pg/mg total brain protein to about 25 pg/mg total brain protein, from about 25 pg/mg total brain protein to about 40 pg/mg total brain protein, from about 40 pg/mg total brain protein to about 60 pg/mg total brain protein, from about 60 pg/mg total brain protein to about 80 pg/mg total brain protein, from about 80 pg/mg total brain protein to about 100 pg/mg total brain protein, from about 100 pg/mg total brain protein to about 125 pg/mg total brain protein, from about 125 pg/mg total brain protein to about 150 pg/mg total brain protein, from about 150 pg/mg total brain protein to about 175 pg/mg total brain protein, from about 175 pg/mg total brain protein to about 200 pg/mg total brain protein, from about 200 pg/mg total brain protein to about 250 pg/mg total brain protein, from about 250 pg/mg total brain protein to about 300 pg/mg total brain protein, from about 300 pg/mg total brain protein to about 500 pg/mg total brain protein, to greater than about 500 pg/mg total brain protein. In a preferred embodiment, the therapeutically effective amount may be greater than about 75 pg/mg total brain protein.

Formulations for intranasal administration of a compound that activates the leptin receptor may comprise from about 5 µg/kg body weight of the subject to about 5000 µg/kg body weight of the subject. In particular, an intranasal formulation may comprise from about 5 µg/kg body weight to about 10 µg/kg body weight, from about 10 µg/kg body weight to about 20 µg/kg body weight, from about 20 µg/kg body weight to about 40 µg/kg body weight, from about 40 µg/kg body weight to about 60 µg/kg body weight, from about 60 µg/kg body weight to about 80 µg/kg body weight, from about 80 µg/kg body weight to about 100 µg/kg body weight, from about 100 µg/kg body weight to about 150 µg/kg body weight, from about 150 µg/kg body weight to about 200 µg/kg body weight, from about 200 µg/kg body weight to about 250 µg/kg body weight, from about 250 µg/kg body weight to about 300 µg/kg body weight, from about 300 µg/kg body weight to about 400 µg/kg body weight, from about 400 µg/kg body weight to about 500 µg/kg body weight, from about 500 µg/kg body weight to about 600 µg/kg body weight, from about 600 µg/kg body weight, to about 700 µg/kg body weight, from about 700 µg/kg body weight to about 800 µg/kg body weight, from about 800 µg/kg body weight to about 900 µg/kg body weight, from about 900 µg/kg body weight to about 1000 µg/kg body weight, from about 1000 µg/kg body weight to about 2000 µg/kg body weight, from about 2000 µg/kg body weight to about 3000 µg/kg body weight, from about 3000 µg/kg body weight to about 4000 µg/kg body weight, from about 4000 μg/kg body weight to about 5000 μg/kg body weight, or more than about 5000 μg/kg body weight. In a preferred embodiment, an intranasal formulation may comprise at least about 800 μg/kg body weight. In determining the therapeutically effective amounts, one skilled in the art will also consider the existence, nature, and extent of any adverse effects that accompany the administration of a particular compound in a particular subject.

Advantageously, a compound that activates the leptin receptor may also be self administered. In an exemplary embodiment, a subject who subjectively recognizes a sub clinical condition that in their experience leads to a seizure may self-administer a compound that activates the leptin receptor intranasally, thereby inhibiting a seizure.

Assays to determine levels compounds that activate the leptin receptor in biological fluids or tissues are well know in the art and include by way of non-limiting example, Enzyme-Linked ImmunoSorbent Assays (ELISA) described below.

DEFINITIONS

As used herein, "subject" refers to a mammal capable of experiencing seizures. Subjects may include humans, mice, rats, or guinea pigs. In some embodiments, subjects may be diagnosed with a seizure disorder, may be at risk for a seizure disorder, or may be experiencing a seizure. Subjects may be of any age including new born, adolescent, adult, middle age, or elderly.

As used herein, "administering" is used in its broadest sense to mean contacting a subject with a compound.

As used herein, "a compound that activates the leptin receptor" is used to describe leptin of any mammal, or variants thereof, or fragments thereof, including synthetic peptides thereof, as well as non-peptide analogs thereof, that bind to and activate leptin receptors such that the janus kinase 2 (JAK2) and/or the phosphoinositide 3-kinase (PI3K) signaling pathways are activated.

EXAMPLES

Leptin or compounds that activate the leptin receptor are useful as clinical anticonvulsants since they can be administered intranasally, such that brain leptin, or levels of compounds that activate the leptin receptor, increases and inhibits focal and generalized seizures. The inventors have shown that leptin is an effective anticonvulsant in vivo using two rodent models, and have examined its effect on evoked synaptic responses in hippocampal slices. These models encompass models generally accepted in the art as models for human seizures. Leptin inhibited focal seizures in rats produced by neocortical injections of 4-aminopyridine (4AP). In CD-1 mice, intranasal leptin administration increased serum and brain leptin levels, and inhibited pentylenetetrazole-induced generalized convulsive seizures. In mouse hippocampal slices leptin selectively inhibited the α-amino-3-hydroxy-5-methyl-4-isoxazole-proprionic acid receptor (AMPAR)-mediated component of evoked Schaffer collateral extracellular field excitatory postsynaptic potentials (fEPSPs) and whole-cell excitatory postsynaptic currents (EPSCs) in a U-shaped, concentration-dependent manner. With a similar dose-dependence, leptin decreased spike frequency in cultured hippocampal neurons induced to burst by removing extracellular magnesium. Leptin did not inhibit the fEPSP in hippocampal slices preincubated with the JAK2 inhibitor AG490 or the PI3K inhibitors LY294002 and wortmannin implicating a JAK/PI3K mediated mechanism. In hippocampal slices from obese, leptin receptor deficient db/db mice, leptin failed to inhibit Schaffer collateral fEPSPs. Leptin receptor activation has anticonvulsant effects that may be exploited to develop better drugs for the treatment of epilepsy.

Methods and Materials for Examples 1-9

Animals. Male Sprague-Dawley rats, Swiss-Webster mice and CD-1 mice were purchased from Charles River Laboratories (Wilmington, Mass.). Male db/db (Stock #000642) and C57BLKS/J (Stock #000662) mice were purchased from Jackson Laboratory (Bar Harbor, Me.). Animal care and experimentation conformed to the PHS Guide for Care and Use of Laboratory Animals and the AVMA Panel on Euthanasia Guidelines, and were approved by the Washington University School of Medicine Animal Studies Committee.

Tissue preparation for electrophysiology. Primary dissociated hippocampal cultures were prepared from E15 Swiss-Webster mouse embryos on glass coverslips with preapplied glial feeder layers as described (Thio et al., 2003). Cells were used for patch-clamp recordings between 9-14 days in vitro. Hippocampal slices were prepared as described previously (Thio et al., 2000), from 6-8 week old mice for extracellular recordings and 3 week old mice for whole-cell recording. Mice were sacrificed under halothane approximately the same time each morning due to leptin's diurnal variation. Brains were rapidly removed, placed in ice-cold ACSF consisting of (in mM): 124 NaCl, 5 KCl, 2.5 $CaCl_2$, 1.3 $MgCl_2$, 1.3 $NaH_2PO_4$, 22 $NaHCO_3$, 10 glucose, saturated with 95% $O_2$/5% $CO_2$ to pH=7.4. Transverse hippocampal slices (400 μm) were prepared with a vibratome and incubated at least 1 hour in ACSF at room temperature before recording experiments.

Materials. Recombinant mouse leptin, D-2-amino-5-phosphonovaleric acid (D-APV), and the disodium salt of 6-cyano-7-nitroquinoxaline-2,3-dione (CNQX) were purchased from Sigma-Aldrich Co. (St. Louis, Mo.). AG490, LY294002, and wortmannin were obtained from Calbiochem (Lajolla, Calif.). Leptin stock solution consisted of one mg of lyophilized leptin solubilized in 0.5 ml of 15 mM HCl followed by addition of 0.3 ml of 7.5 mM NaOH to raise the pH to ~5.2. The resulting stock solution was diluted in artificial cerebrospinal fluid (ACSF) for cortical injection or in vitro electrophysiology experiments. To enhance CNS absorption after intranasal leptin administration (Shimizu et al., 2005), 1 mg lysophosphatidylcholine (LPC, Sigma-Aldrich Co., St. Louis, Mo.) was dissolved in 0.2 ml 0.9% saline and mixed with 0.8 ml of the leptin stock solution, final concentration 1 mg/ml leptin, 0.1% LPC.

Leptin assay. Serum and brain leptin levels were measured using a commercial mouse ELISA kit (EZML-82K, Linco Research/Millipore Corp, Billerica, Mass.). Leptin standards containing concentrations below 1 ng/ml were indistinguishable from the blanks, indicating that the lower limit of detection is 1 ng/ml leptin. Therefore, all samples having readings below the average+3 standard deviations (SD) for a blank were considered to have an undetectable leptin level, i.e. <1 ng/ml leptin. Brain or serum samples with higher than the maximum quantifiable level of leptin were diluted with assay buffer to obtain measurements within the range of the leptin standards in the kit, and values were calculated using the appropriate dilution factor.

Mice were deeply anesthetized and then thoracotomy was performed to expose the heart. Blood was obtained by right atrium puncture and centrifuged. Next, intracardiac perfusion was performed via the left ventricle using cold (0-4° C.) PBS for 5-7 minutes, followed by brain removal. Pieces of frontal-parietal cerebral cortex and serum samples were immediately frozen on dry ice and stored at −80° C. until processed. Brain leptin levels were measured in some animals receiving PTZ. These animals were not perfused, but control experiments demonstrated that the leptin from the blood remaining in the non-perfused brain did not produce detectable brain leptin levels.

The leptin ELISA was performed on brain and serum samples according to the manufacturer's instructions. Brain levels were measured in samples (~30-50 mg) prepared by mixing with 10 µL of lysis buffer per mg tissue. Lysis buffer consisted of 160 mM KCl, 25 mM HEPES, and 1% Triton-X 100. Samples were sonicated and mixed on a micro-rotator for 1 hour, followed by centrifugation for 20 min at 4° C. at 14,000 rpm. The supernatant was stored at −80° C. until analyzed. For leptin measurements, different dilutions of supernatant were made with assay buffer from the kit. Leptin levels in these samples of brain tissue were normalized to protein levels, which were determined using a commercially available kit (Micro BCA Protein Assay Kit, Pierce Biotechnology, Inc., Rockford, Ill.). All measurements were done in triplicate.

Neocortical seizure model. Four to six week old male Sprague-Dawley rats were anesthetized with halothane (4%) and then placed on stereotaxic frame (David Kopf Instruments, Tujunga, Calif.). A burr hole was drilled over the left hemisphere at a site 2 mm anterior to the bregma and 2.5 mm lateral to midline using a dental drill. After surgery, halothane was reduced to 1-2% and 1 µl ACSF containing 12.5 mM 4-aminopyridine (4AP, 12.5 nanomoles) was injected from a glass micropipette (tip diameter, ~100 µm) into the motor cortex 0.5 mm deep to the cortical surface with a commercial injector (Nanoject, Drummond Scientific, Broomall, Pa.). This model produces frequent, repetitive seizures narrowly localized to the site of injection (Yang and Rothman, 2001). Leptin-treated rats were injected with 1 µl ACSF containing 12.5 mM 4AP and 39 µM leptin (39 picomoles). Two screw electrodes were placed symmetrically over each hemisphere and differentially recorded the electroencephalogram (EEG) in a referential montage, using standard AC EEG amplifiers (Grass-Telefactor, West Warwick, R1). The EEG was digitized (200 Hz) and stored using PC based commercial hardware (Digidata and Axoscope, Axon Instruments, Union City, Calif.). EEG recordings started 15 minutes before and ended 90 minutes after the 4AP injection. The EEG was visually analyzed by a blinded reviewer to determine the number of seizures in a record and seizure duration. A seizure was defined as a discrete electrographic event with an onset consisting of low amplitude, high frequency discharge followed by an evolving rhythmic, repetitive high amplitude discharge with a distinct termination.

Pentylenetetrazole (PTZ) generalized seizure model. Six to eight week old male CD-1 mice were divided into a vehicle-treated control group and a leptin-treated group. A 20 mg/ml PTZ stock was made using sterile 0.9% saline, and each mouse received 75 mg/kg PTZ via an intraperitoneal (IP) injection. Leptin-treated rats received 8, 80, or 800 µg/kg in 0.1% LPC intranasally (IN), 30 minutes before PTZ administration. Control mice received LPC vehicle without leptin, IN. All mice, regardless of the leptin dose administered, received a total volume of 20 pl. An observer blinded to the treatment administered, measured the latency to the onset of the first generalized convulsive seizure as assessed behaviorally.

Electrophysiology experiments. Hippocampal slices were transferred to a submerged recording chamber (Warner Instruments, Hamden, Conn.) and perfused continuously at a rate of 3 ml/min with ACSF (see above) at 30° C. Field excitatory postsynaptic potentials (fEPSPs) were recorded from CA1 stratum radiatum using glass electrodes filled with 2 M NaCl (resistance 3-5 MΩ). EPSPs were evoked by stimulation of the Schaffer collateral pathway through a bipolar electrode (David Kopf Instruments, Tujunga, Calif.) at a frequency of 0.0167 Hz. In all experiments, a stimulus intensity that evoked an EPSP having 50% of the maximal slope was used. The fEPSP slopes obtained during 15-20 minutes of stable baseline recording were averaged, and then used to normalize fEPSP slopes during drug application and washout, in order to combine data from different brain slices. Evoked whole-cell excitatory postsynaptic currents (EPSCs) were recorded in voltage-clamp configuration from individual CA1 pyramidal neurons in hippocampal slices prepared as above from P21-28 male CD-1 mice. Neurons were identified using infrared DIC video microscopy (Wong et al., 2003). ACSF was slightly modified for whole-cell recording in slices, containing 2 mM $CaCl_2$ and 1 mM $MgCl_2$. NMDAR-mediated EPSCs were isolated by adding 10 µM NBQX. Patch electrodes for slice recording were filled with an internal solution containing (in mM) 140 potassium gluconate, 5 NaCl, 1 $CaCl_2$, 2 MgATP, 10 EGTA, 10 HEPES, pH 7.3. Whole-cell recording from hippocampal neuron cultures were performed using an internal solution containing (in mM) 140 potassium gluconate, 4 NaCl, 0.5 $CaCl_2$, 2 MgATP, 0.5 $Na_2GTP$, 5 EGTA, 10 HEPES, pH 7.2, and an external solution containing (in mM) 140 NaCl, 5 KCl, 1.5 $CaCl_2$, 1 $MgCl_2$, 10 HEPES, 10 glucose, pH 7.3. Analog data were obtained using an Axopatch 200B amplifier, digitized at 10 kHz and analyzed using Axon Instruments Digidata 1322A and pClamp9 (Molecular Devices, Foster City, Calif.).

Statistical analyses. All data are presented as the mean±standard deviation (SD). Statistical analyses were performed using paired or unpaired t-test with appropriate corrections as indicated; ANOVA with Tukey-Kramer post test or Kruskal-Wallis with Dunn's post test were used for comparisons between multiple groups. Statistical significance was set at $p < 0.05$.

Example 1

Leptin Inhibits 4AP Induced Neocortical Seizure in Rats

Figure 1:
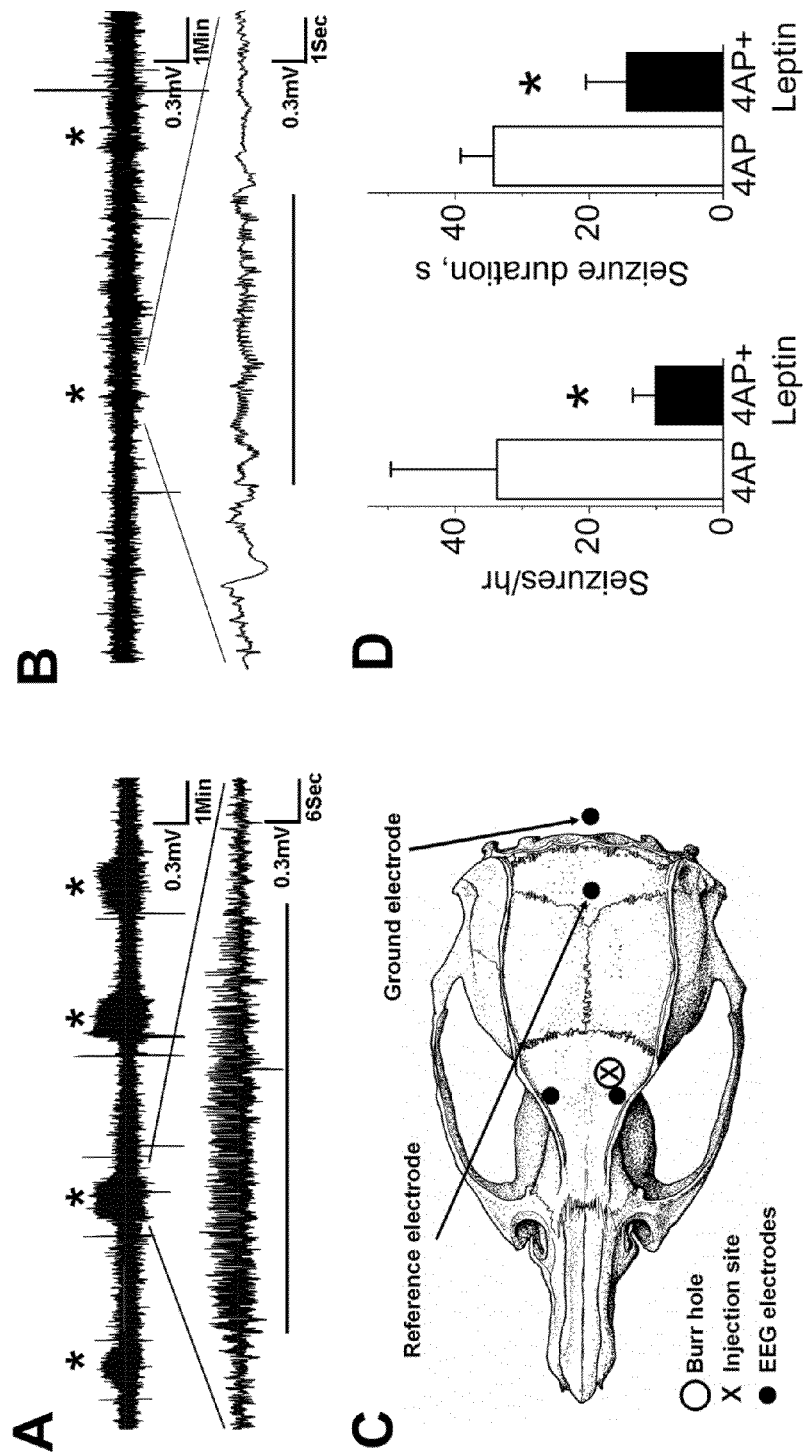
FIG. 1 depicts the inhibition of focal neocortical seizures induced by 4-aminopyridine (4AP) injections into the left motor cortex by leptin. A, Top trace—15 min EEG segment recorded from the frontal area ipsilateral to the injection site 45 min after injecting 12.5 nanomoles of 4AP. Asterisks indicate 4 individual seizures. Bottom trace—a one min seizure at an expanded time base to illustrate the electrographic details of the seizure (underlined). B, Top trace—15 min EEG segment recorded 45 min after injection of 12.5 nanomoles of 4AP+39 picomoles of leptin shows two shorter, lower amplitude seizures (asterisks). Bottom trace—a 10 sec seizure shown at an expanded time base (underlined). Note different time calibration for bottom trace compared to A. C, Location of the burr hole, injection site, and recording electrode locations relative to standard landmarks. D, Leptin reduces frequency and duration of 4AP induced seizures. Seizure frequency (left panel) and duration (right panel) in rats injected with 12.5 nanomoles of 4 AP alone (open bars, n=5) or 12.5 nanomoles+39 picomoles of leptin (filled bars, n=5). Seizure frequency and duration for each rat were determined from the 60 min of EEG collected between 30 and 90 min after 4AP injection. (*) $p<0.02$ for frequency vs. 4AP alone and $p<0.001$ for duration vs. 4AP alone by unpaired t-test.

4AP, a nonspecific inhibitor of voltage-gated $K^+$ channel, induced seizures that were easy to identify electrographically by their discrete onset, stereotypically evolving amplitude and frequency features, and abrupt cessation (FIG. 1A). Electrographic seizures in rats co-injected with 12.5 nanomoles of 4AP+39 picomoles of leptin were lower amplitude and noticeably briefer and less frequent compared to the rats injected with 12.5 nanomoles of 4AP+vehicle (FIG. 1, B and D). Leptin decreased the cumulative seizure duration, defined as the total duration of ictal activity between 30 and 90 min post 4AP injection, from 19±9.3 min (n=5) to 2.6±1.7 min (n=5, $p < 0.001$, t-test). Leptin did not eliminate interictal spikes.

Example 2

Intranasal Leptin Administration and Pentylenetetrazole-Induced Seizures

Figure 2:
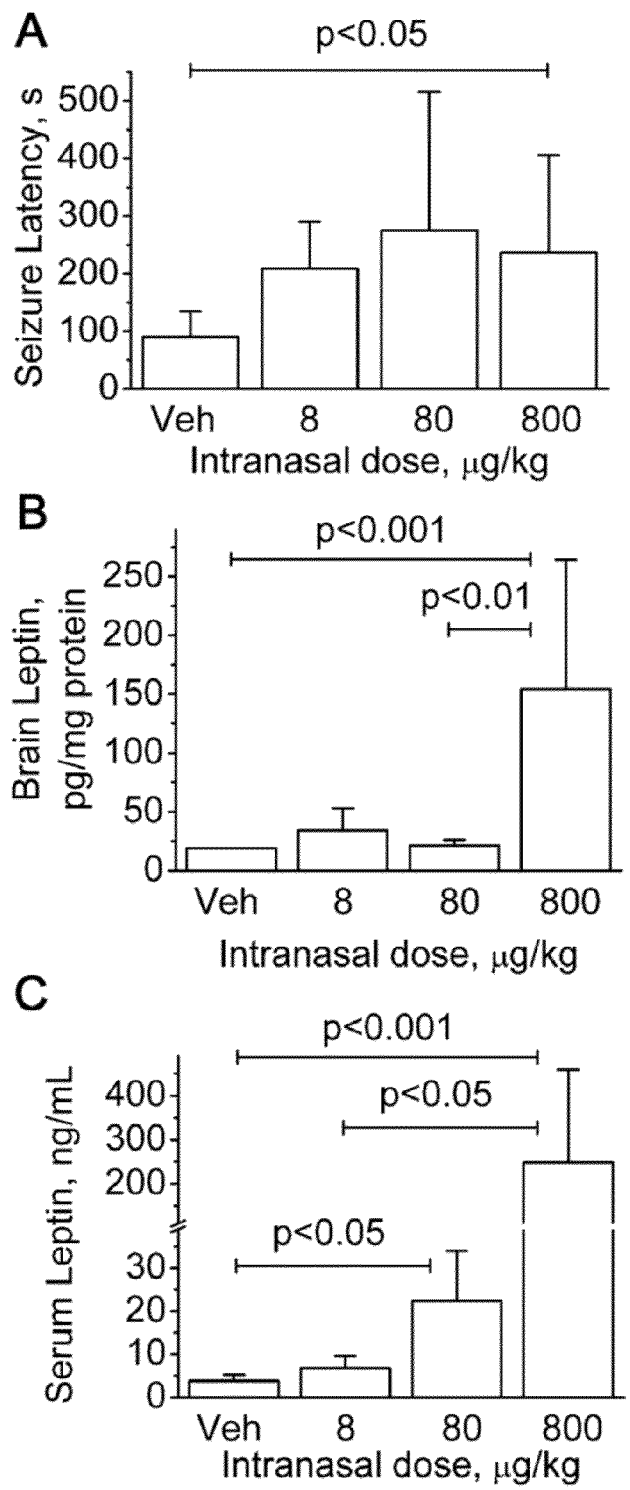
FIG. 2 depicts the inhibition of pentylenetetrazole-induced generalized convulsive seizures, and the elevation of serum and brain leptin levels by intranasal administration of leptin.

Pentylenetetrazole (PTZ), a γ-aminobutyric acidA receptor (GABAAR) antagonist is a chemical convulsant that reliably produces generalized convulsive seizures (clonic-tonic) when administered intraperitoneally (IP). The rodent PTZ seizure model has a quantifiable seizure onset latency, easily recognized behavioral seizures, and predictive value for anticonvulsant efficacy against generalized seizures in humans. Therefore, the PTZ model is a standard animal seizure model according to the NIH/NINDS Anticonvulsant Drug Development (ADD) Program (Stables et al., 2002). To determine if leptin inhibits seizures in this model, the inventors gave leptin intranasally (IN) to CD-1 mice 30 minutes before giving 75 mg/kg PTZ IP. A leptin dose of 800 µg/kg more than doubled the seizure latency compared to control (FIG. 2A). Leptin doses of 8 and 80 µg/kg also increased seizure latency, but the differences were not statistically significant (FIG. 2A, 2B). Leptin was not a proconvulsant at the three doses utilized.

Example 3

Brain and Serum Leptin Levels After IN Leptin Administration

The inventors observed that serum and brain leptin levels increased 30 minutes after IN leptin administration. Dramatic increases in serum and brain leptin levels occurred 30 minutes after an 800 µg/kg IN leptin administration (FIG. 2B, 2C). Leptin doses of 8 and 80 µg/kg produced smaller increases in serum and brain leptin levels. All brains of mice receiving 800 µg/kg leptin showed leptin levels above 20 pg/mg protein. The brains of some mice receiving 8 and 80 µg/kg leptin showed levels below 20 pg/mg protein. All vehicle treated mice had brain leptin levels below 20 pg/mg protein.

Serum and brain leptin levels varied with the type of anesthesia used during the IN leptin administration. Brain and serum leptin levels were lower when leptin was administered with halothane compared to ketamine anesthesia for technical reasons. Inhaled halothane anesthesia had to be discontinued during IN leptin administration. Consequently, the inhaled anesthesia began to reverse during IN leptin administration, and the mice swallowed or expelled some of it. For the PTZ experiments, the inventors used halothane rather than ketamine anesthesia during the IN leptin administration because the mice did not recover from ketamine anesthesia within 30 minutes and because ketamine has anticonvulsant activity.

Example 4

Leptin Inhibits Synaptic Responses in Mouse Hippocampal Slices

In hippocampal slices, leptin enhances NMDAR mediated responses and converts STP to LTP (Shanley et al., 2001). This effect is unlikely to account for our observation that leptin reduces 4AP induced seizures. However, Shanley et al. (2001) also observed modest, reversible inhibition of AMPAR mediated excitatory postsynaptic currents (EPSCs) without alteration of the cell input resistance, raising the possibility that AMPAR inhibition could partially explain leptin's anticonvulsant action. The absence of reduced input resistance would argue against increased tonic activity of ion channels such as BK or KATP. Therefore, the inventors examined the effect of leptin on CA1 stratum radiatum fEPSPs evoked by Schaffer collateral stimulation in hippocampal slices. Fifteen minutes after bath applying 0.6 nM leptin, a reversible, 81±6% (n=7 slices, 6 mice) reduction occurred in the slope of the fEPSP (FIGS. 3A and 3B). Leptin produced a U-shaped, concentration-dependent inhibition of the fEPSP slope with 50 nM leptin producing only a 4±7% reduction in the slope (n=6 slices, 2 mice) (FIG. 3C).

Example 5

Leptin Selectively Inhibits the AMPAR Component of the fEPSP and Increases Paired Pulse Facilitation To evaluate whether leptin differentially inhibited AMPARs and NMDARs, the inventors pharmacologically isolated these components and examined leptin's effects. The CA1 fEPSP slope in nominally $Mg^{2+}$ free (no added) ACSF was 97.0±4% (n=4 slices, 1 mouse) of the baseline response obtained in standard ACSF. In the same slices, the fEPSP slope was reduced to 26±6% of the baseline response by adding 10 µM CNQX to the ACSF to block the AMPAR-mediated component of the fEPSP, and the fEPSP slope was further reduced to 5±2% of the baseline response by combined application of ACSF with 10 µM CNQX and 50 µM D-APV, an NMDAR antagonist. In ACSF with 50 µM D-APV, 0.6 nM leptin inhibited the isolated AMPAR component of the fEPSP (fEPSP slope after 30 min of leptin application was 26±2% of baseline, n=4 slices, 2 mice, FIG. 4A). In $Mg^{2+}$ free ACSF with 10 µM CNQX, leptin did not affect the isolated NMDAR component of the fEPSP (FIG. 4B).

The selective inhibition of the AMPAR component of the fEPSP generally supports a postsynaptic mechanism. To further distinguish between a pre- and postsynaptic site of action, the inventors examined the effect of leptin on paired pulse facilitation. The inventors compared the paired pulse ratio (P2/P1, where P1 is the slope of the first fEPSP and P2 is the slope of the second fEPSP) at baseline and after applying 0.6 nM leptin for 20 minutes. Leptin reduced the slope of both fEPSPs in a pair (FIG. 4C, arrows), and slightly but significantly increased the paired pulse ratio (FIG. 4D), suggesting an additional presynaptic inhibitory mechanism.

Given that the above results do not definitively support a presynaptic mechanism, the inventors used whole-cell voltage clamp recordings from CA1 pyramidal neurons to examine the effect of leptin on AMPAR and NMDAR-mediated EPSCs. Leptin inhibited AMPAR-mediated EPSCs and fEPSPs in a similar manner except that only partial recovery occurred with washout (FIG. 5A). Leptin at 0.6 nM reduced the amplitude of AMPAR EPSCs recorded at −70 mV by 56±20% (n=9) with a lower and a higher concentration producing no change (FIG. 5B). In two other cells 0.6 nM leptin did not inhibit the AMPAR-mediated EPSC and these cells were not included in the analysis. Leptin produced a larger increase in paired-pulse facilitation of AMPAR mediated EPSCs than of fEPSPs (FIG. 5C). In eight of eleven cells leptin also significantly lengthened the EPSC latency from 3.2±0.5 ms to 4.3±1.0 (p=0.013 paired t-test), with partial recovery to baseline on leptin wash out. Of the three cells that exhibited no change in EPSC latency, leptin clearly inhibited the EPSC in two. The average amplitude of NMDAR-mediated EPSCs recorded at +20 mV in ACSF containing 2 mM $CaCl_2$, 1 mM $MgCl_2$, and 10 µM NBQX (selective AMPAR antagonist) was 97±3.2% of control (n=5 cells). Together these results suggest that leptin inhibits AMPAR mediated synaptic transmission pre- and postsynaptically.

Example 6

Leptin Inhibits Low Magnesium-Induced Spiking in Cultured Hippocampal Neurons

To determine whether leptin reduced neuronal hyperexcitability at concentrations comparable to those that inhibit AMPAergic EPSPs and EPSCs in slices, the inventors examined the effect of leptin on the bursts of action potential induced in cultured hippocampal neurons by a nominally $Mg^{2+}$ free extracellular solution (Mangan and Kapur, 2004; Goodkin et al., 2005). Cultured hippocampal neurons generally fire isolated action potentials when $Mg^{2+}$ is present in the extracellular solution. When the extracellular contains no added $Mg^{2+}$, the neurons fire bursts of action potentials superimposed upon a depolarizing wave that resembles a paroxysmal depolarizing shift (FIG. 6A1). Leptin decreased action potential bursting (FIG. 6A2, 1 nM leptin), that partially reverted to baseline spike frequency after leptin wash out (FIG. 6A3). Cumulative data show that one and ten nM leptin, but not 0.1 nM leptin, significantly decreased action potential bursting as assessed by comparing spike frequency in the same neuron before and after leptin application (FIG. 6B). Thus, leptin decreases neuronal hyperexcitability in cultured hippocampal neurons in the same concentration range that decreases AMPAR mediated EPSCs in hippocampal slices.

In separate experiments the inventors examined whether leptin altered neuronal input resistance or action potential properties. The inventors used cultured hippocampal neurons because they are more compact electrically making leptin induced changes in input resistance easier to detect.

Neuronal input resistance and action potential characteristics were evaluated in current clamp configuration by subjecting cultured hippocampal neurons to a series of 700 ms hyperpolarizing and depolarizing current steps ranging from −40 pA to +40 pA in 10 pA increments. Action potential amplitude, duration, and threshold were analyzed for each neuron before and after application of different concentrations of leptin (0.1-10 nM). Action potential amplitude was defined as the difference between the peak voltage of the action potential and the resting membrane potential. Duration was defined as the action potential width at half amplitude. Threshold was defined as the voltage during the rising phase of the action potential at which dV/dt reaches 2% of its maximum (Khaliq and Raman, 2006). Neuronal input resistance was determined by the slope of the line obtained by plotting membrane voltage 600 ms after the start of a hyperpolarizing current step versus the magnitude of the current step. (Khaliq Z M, Raman I M (2006) J Neurosci 26: 1935-1944).

Leptin concentrations ranging from 0.1, 1 and 10 nM had no effect on neuronal input resistance or action potential properties including threshold, amplitude or duration (Table 1).

TABLE 1

Action potential characteristics and neuronal input resistance with leptin.

| | Control Buffer (n = 13) | Leptin, 0.1 nM (n = 5) | Leptin, 1 nM (n = 6) | Leptin, 10 nM (n = 6) |
|---|---|---|---|---|
| Duration at half-maximal amplitude, ms | 2.3 ± 0.8 | 2.2 ± 0.6 | 1.7 ± 0.5 | 2.6 ± 0.8 |
| Spike threshold, mV | −38 ± 6.9 | −36 ± 8.3 | −38 ± 5.8 | −38 ± 7.1 |
| Input resistance, MΩ | 1026 ± 404 | 948 ± 452 | 1237 ± 409 | 907 ± 359 |

Example 7

JAK and PI3K Inhibitors Prevent Leptin Inhibition of the fEPSP

Leptin receptors are class I cytokine receptors that signal via association with janus tyrosine kinases (JAKs). When leptin binds to the long form of the leptin receptor, Ob-Rb, JAK2 is activated and both proteins are subsequently phosphorylated, recruiting and activating downstream signaling pathways in hematopoetic, adipocyte, pancreatic and muscle cells (Fruhbeck, 2006 Bjorbaek and Kahn, 2004). There is evidence indicating that JAK/PI3K signaling is important in neurons (Barnabe-Heider et al., 2005; Yadav et al., 2005; Qiu et al., 2005), and leptin mediated effects in neurons have been inhibited by JAK inhibitors (Hsu et al., 2006; Russo et al., 2004; Dicou et al., 2001) and PI3K inhibitors (O'malley et al., 2005; Shanley et al., 2002b).

Therefore, the inventors examined whether JAK and PI3K inhibitors would prevent leptin from decreasing CA1 fEPSPs. After obtaining baseline EPSP recordings, application of the JAK2 inhibitor AG490 alone (20 μM; 45-60 min) had no effect on the fEPSP slope. However, pre-incubating slices with AG490 for at least 3 hours prevented 0.6 nM leptin from inhibiting CA1 fEPSPs (FIG. 7A). the inventors also used two structurally unrelated PI3K inhibitors, LY294002 and wortmannin, to investigate whether PI3K activation is necessary for leptin's effect. Application of LY294002 (16 μM) or wortmannin (50 nM) alone had no effect on baseline fEPSP slope. Pre-incubation with either agent at least 3 hours completely prevented leptin-induced inhibition of fEPSPs (FIG. 7B, C). These data indicate that leptin-induced inhibition of CA1 hippocampal AMPAR synaptic responses requires activation of the JAK2-PI3K signaling pathway.

Example 8

Effects of Leptin in db/db Mice

Leptin acts systemically to orchestrate complex biological effects through its specific cellular receptor. As mentioned above, the long form of the leptin receptor (Ob-Rb) is capable of full signal transduction. To address whether leptin inhibition of AMPAR mediated synaptic responses requires leptin receptor activation, the inventors compared the effects of leptin on CA1 fEPSPs in hippocampal slices from db/db mice, which are Ob-Rb deficient (Chen et al., 1996), and wild-type C57BLKS/J mice, the background strain of db/db mice. In slices from C57BLKS/J mice, leptin inhibited synaptic responses as observed in CD-1 mice; CA1 fEPSP slopes were 34±3% (n=6 slices, 3 mice) of baseline after perfusing 0.6 nM leptin for 30 min (FIG. 8). However, in slices from db/db mice, leptin did not alter CA1 fEPSP slopes with the slopes being 93±12% (n=10 slices, 3 mice) of baseline after applying 0.6 nM leptin for 30 min. This result indicates that Ob-Rb activation is necessary for leptin to inhibit AMPAR mediated CA1 hippocampal synaptic responses.

Example 9

Intranasal Leptin Administration in ob/ob and db/db Mice

Figure 9A:
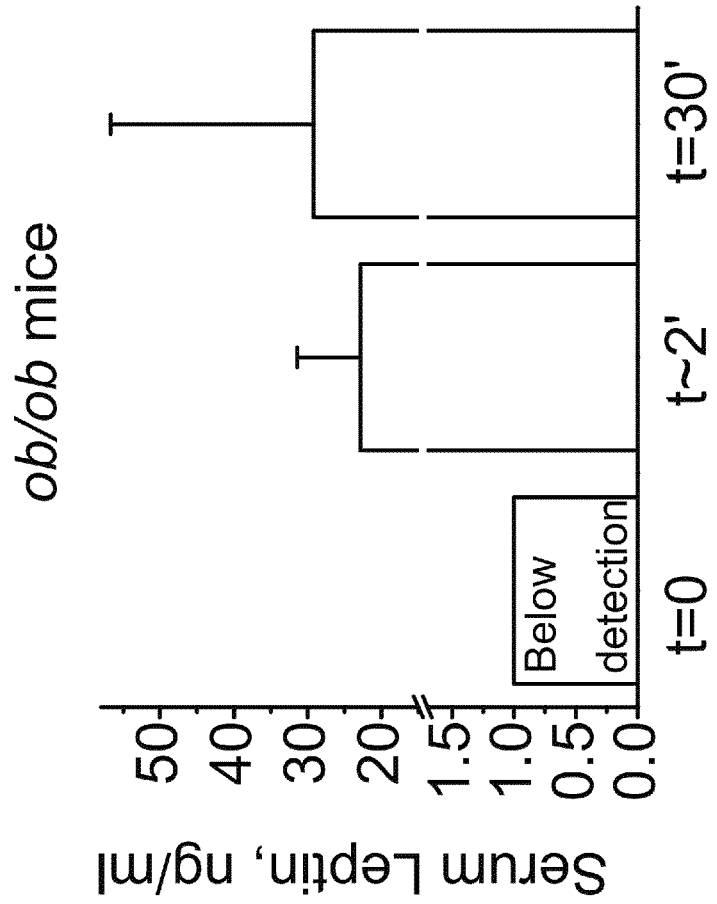
Figure 9B:
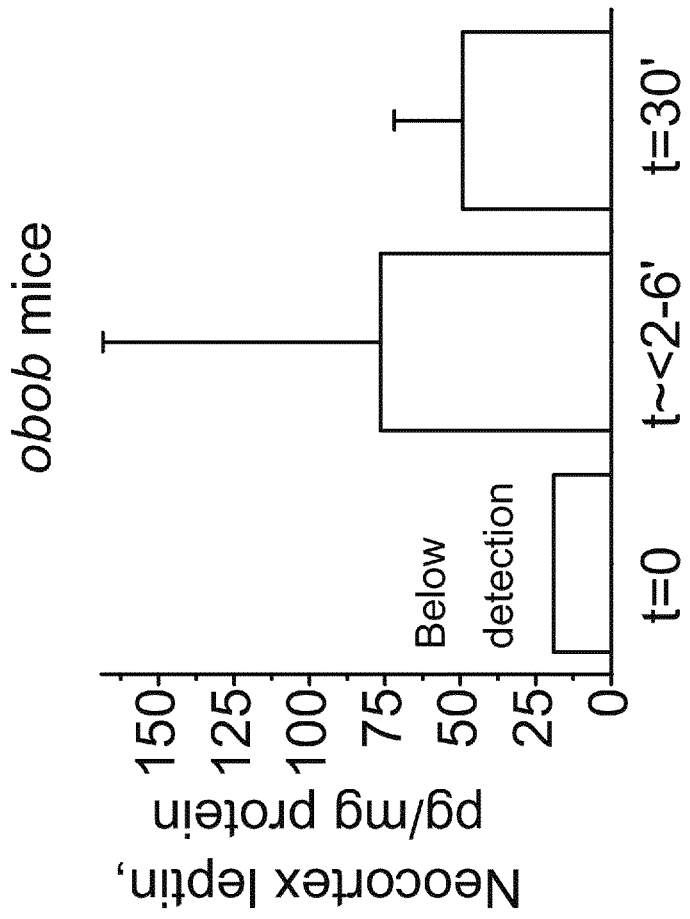

A rapid increase of leptin in the serum and brain of mice was seen after leptin was administered intranasally. Leptin was administered intranasally (800 μg/kg) to mice deficient in leptin (ob/ob). Increased leptin in the serum was seen as early as 2 minutes, which persisted at 30 minutes (FIG. 9A). A rapid increase of leptin in the brain was also seen at 2 and 30 minutes under the same conditions (FIG. 9B). These results indicate that intranasal administration enables leptin to reach the brain and serum in a manner that is rapid and sustainable.

Figure 9C:
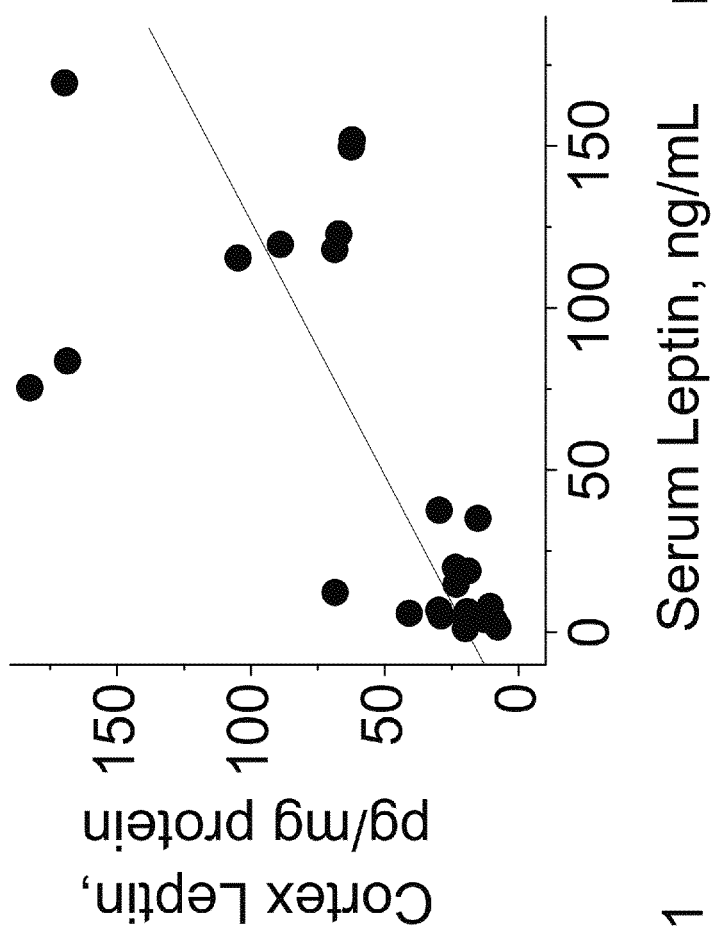

Leptin, when administered intranasally reaches the brain directly. Mice that are deficient in leptin receptors (db/db) have a compensatory elevation in serum leptin compared to wild type (C57) mice (FIG. 9C). After intranasal administration of leptin (800 μg/kg), serum leptin levels are further elevated (FIG. 9C, db/db+lep). Despite very high levels of serum leptin, brain leptin in db/db mice is indistinguishable from wild type mice (FIG. 9D). However, after intranasal administration of leptin, brain leptin increases (FIG. 9D, db/db+lep). These results indicate that intranasal administration enables leptin to bypass the reduced entry limitations of leptin from serum to brain.

Example 10

Intranasal Leptin Administration in Normal Mice

Figure 12A:
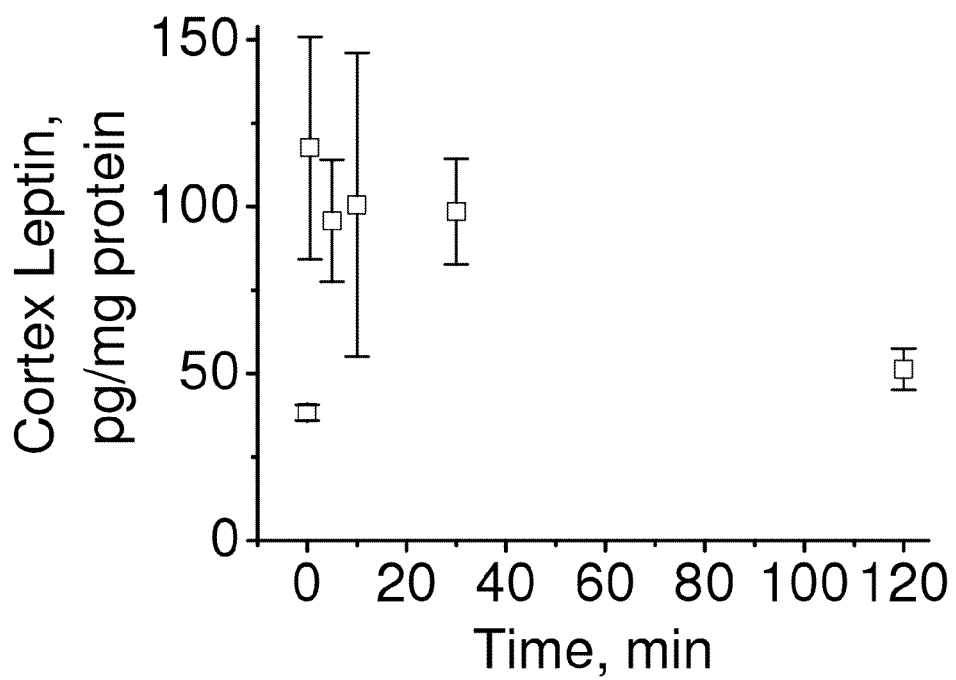
Figure 12B:
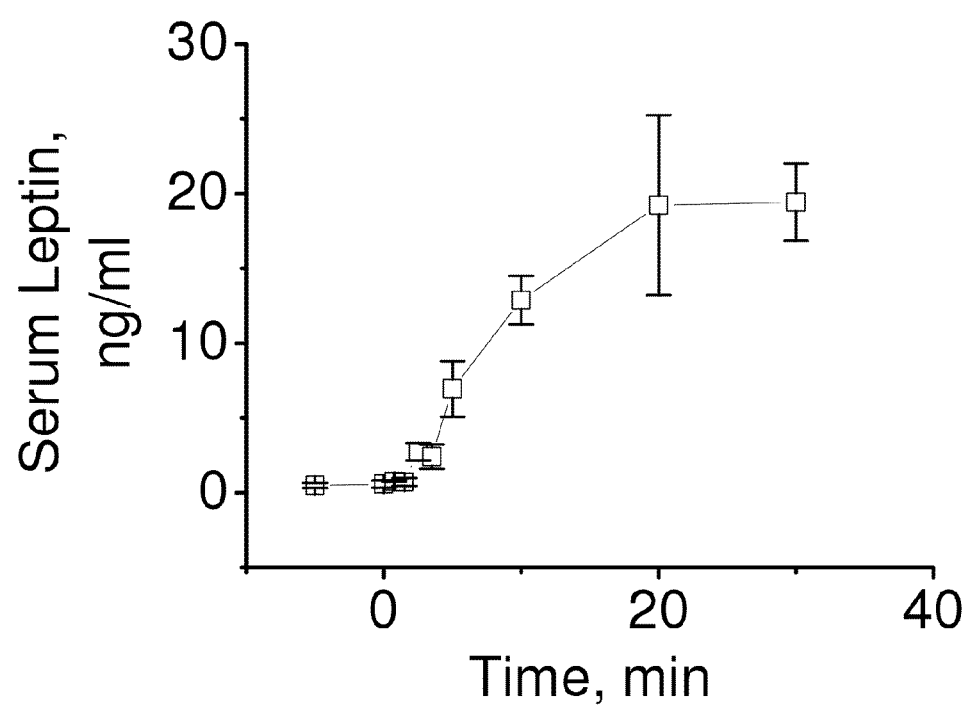
Figure 12C:
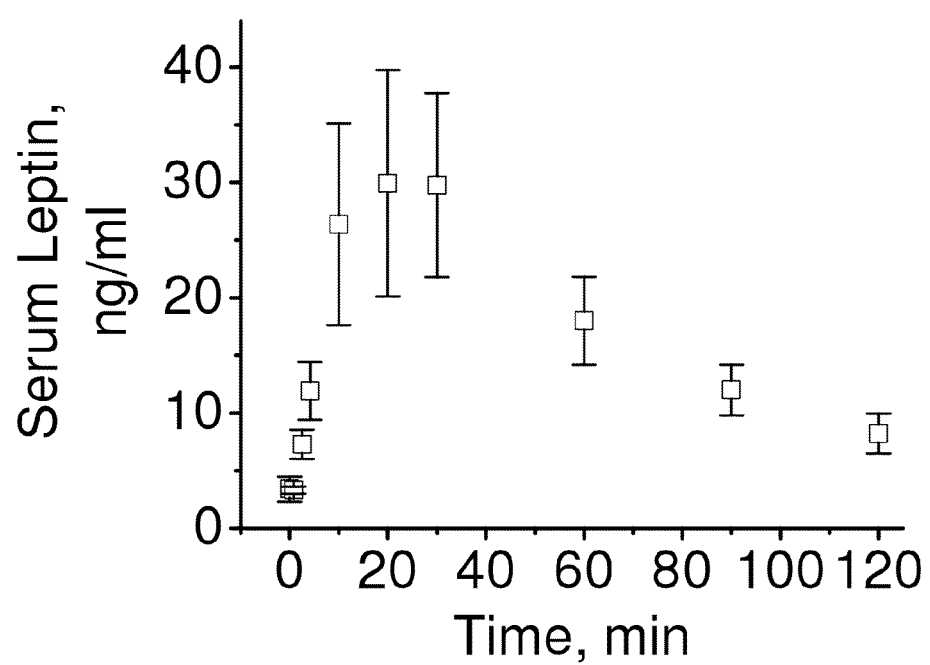
Figure 12D:
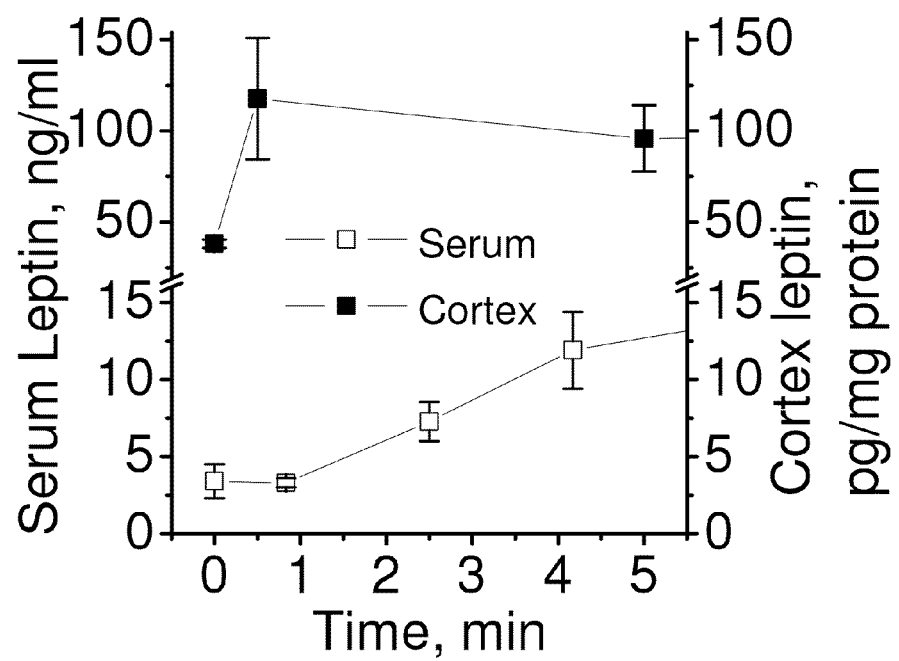

A rapid increase of leptin in the serum and brain of mice was sustained over time following intranasal leptin administration. Leptin was administered intranasally (200 μg/kg) to normal mice. Increased leptin levels in the brain were detected as early as 30 seconds (Table 2), which persisted for 5, 10, and 30 minutes (FIG. 12A and Table 2). The increased levels decreased by 120 minutes, but remained elevated compared to baseline readings taken prior to administration of leptin (FIG. 12A and Table 2). Increased leptin in serum was detected as early as 90 seconds using arterial sampling, which continued to increase up to 2.5 minutes. Serum leptin levels remained elevated over 3.5, 5, 10, 20, and 30 minutes. (FIG. 12B). A rapid increase of serum leptin level was also detected using tail vein blood under the same conditions (FIG. 12C). Both serum and brain leptin levels increased 30 and 90 seconds, respectively, after intranasal administration and remained elevated for 5 minutes (FIG. 12D). These results indicated that intranasal administration enables leptin to reach the brain before the blood in a manner that is rapid and sustainable.

TABLE 2

Cortex leptin levels (pg/mg protein) following 0.2 mg/kg intranasally administered leptin dose.

Cortex leptin levels (pg/mg protein) for 0.2 mg/kg leptin treated

|  | 0 min sal | 30 sec | 5 min | 10 min | 30 min | 120 min |
|---|---|---|---|---|---|---|
|  | 39.8915562 | 68.047154 | 110.89526 | 51.7309617 | 52.45771064 | 66.65829969 |
|  | 44.6763904 | 102.79965 | 54.509784 | 281.291594 | 47.00768792 | 60.11912661 |
|  | 39.5209886 | 246.58429 | 52.341776 | 59.49812098 | 131.4491582 | 65.05925221 |
|  | 36.4566449 | 64.522228 | 116.01595 | 73.00300555 | 57.1856858 | 69.38810374 |
|  | 30.5274412 | 106.13824 | 145.09335 | 37.31020057 | 172.7708907 | 48.84436087 |
| * |  |  |  |  | 126.6568659 | 17.32459701 |
| * |  |  |  |  | 107.9390648 | 42.02580871 |
| * |  |  |  |  | 92.49387255 | 40.84009367 |
| Ave | 38.2146042 | 117.61831 | 95.771221 | 100.5667766 | 98.49511705 | 51.28245531 |
| SD | 5.20711975 | 74.599098 | 40.804045 | 101.8506097 | 44.71818711 | 17.67131192 |
| SEM | 2.32869475 | 33.361731 | 18.248124 | 45.54897738 | 15.81026668 | 6.247752247 |

(* denotes serum leptin levels after same treatment)

TABLE 3

Serum leptin levels (pg/mg protein) following 0.2 mg/kg intranasally administered leptin dose.

Leptin levels (ng/ml) serum

| Time point | 12401 | 12402 | 12403 | Average | SD | SEM |
|---|---|---|---|---|---|---|
| baseline | 0.33995 | 0.3025 | 0.82165 | 0.488033 | 0.289527 | 0.167158 |
| baseline | 0.18275 | 1.0352 | 0.5275 | 0.581817 | 0.428813 | 0.247575 |
| 45 sec | 0.7278 | 0.8719 | 0.7026 | 0.767433 | 0.091344 | 0.052737 |
| 90 sec | 0.2713 | 1.1736 | 0.6963 | 0.713733 | 0.451403 | 0.260617 |
| 2.5 min | 2.4858 | 1.9198 | 3.8384 | 2.748 | 0.985808 | 0.569157 |
| 3.5 min | 1.3299 | 1.8944 | 4.0162 | 2.4135 | 1.416386 | 0.817751 |
| 5 min | 5.8995 | 4.36 | 10.54925 | 6.93625 | 3.222242 | 1.860362 |
| 10 min | 9.665 | 14.1965 | 14.7965 | 12.886 | 2.805554 | 1.619787 |
| 20 min | 12.8775 | 13.5645 | 31.2725 | 19.23817 | 10.4277 | 6.020434 |
| 30 min | 15.079 | 24.035 | 19.1925 | 19.4355 | 4.482942 | 2.588228 |

(12401, 12402, and 12403 indicate 3 different animals; SD denotes standard deviation; and SEM denotes standard error of mean)

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the claims.

REFERENCES

1. Barnabe-Heider F, Wasyinka J A, Fernandes K J, Porsche C, Sendtner M, Kaplan D R, Miller F D (2005) Evidence 1. that embryonic neurons regulate the onset of cortical gliogenesis via cardiotrophin-1. Neuron 48: 253-265.
2. Bjorbaek C, Kahn B B (2004) Leptin signaling in the central nervous system and the periphery. Recent Prog Horm Res 59: 305-331.
3. Chen H, Charlat 0, Tartaglia L A, Woolf E A, Weng X, Ellis S J, Lakey N D, Culpepper J, Moore K J, Breitbart R E, Duyk G M, Tepper R I, Morgenstern J P (1996) Evidence that the diabetes gene encodes the leptin receptor: identification of a mutation in the leptin receptor gene in db/db mice. Cell 84: 491-495.
4. Dicou E, Attoub S, Gressens P (2001) Neuroprotective effects of leptin in vivo and in vitro. Neuroreport 12: 3947-3951.
5. Fruhbeck G (2006) Intracellular signaling pathways activated by leptin. Biochem J 393: 7-20.
6. Goodkin H P, Yeh J L, Kapur J (2005) Status Epilepticus Increases the Intracellular Accumulation of GABAA Receptors. J Neurosci 25: 5511-5520.
7. Hsu H T, Chang Y C, Chiu Y N, Liu C L, Chang K J, Guo I C (2006) Leptin interferes with adrenocorticotropin/3',5'-cyclic adenosine monophosphate (cAMP) signaling, possibly through a Janus kinase 2-phosphatidylinositol 3-kinase/Akt-phosphodiesterase 3-cAMP pathway, to down-regulate cholesterol side-chain cleavage cytochrome P450 enzyme in human adrenocortical NCI-H295 cell line. Clin Endocrinol Metab 91: 2761-2769.
8. Mangan P S, Kapur J (2004) Factors Underlying Bursting Behavior in a Network of Cultured Hippocampal Neurons Exposed to Zero Magnesium. J Neurophysiol 91: 946-957.
9. O'Malley D, Irving A J, Harvey J (2005) Leptin-induced dynamic changes in the actin cytoskeleton mediate the activation and synaptic clustering of BK channels. FASEB J 19:1917-1919.
10. Qiu J, Cafferty W B, McMahon S B, Thompson S W (2005) Conditioning injury-induced spinal axon regeneration requires signal transducer and activator of transcription 3 activation. J Neurosci 25: 1645-1653.
11. Russo V C, Metaxas S, Kobayashi K, Harris M, Werther G A (2004) Antiapoptotic effects of leptin in human neuroblastoma cells. Endocrinology 145: 4103-4112.
12. Shanley L J, Irving A J, Harvey J (2001) Leptin enhances NMDA receptor function and modulates hippocampal synaptic plasticity. J Neurosci 21:RC186: 1-6.
13. Shanley L J, O'malley D, Irving A J, Ashford M L, Harvey J (2002b) Leptin inhibits epileptiform-like activity in rat hippocampal neurones via PI 3-kinase-driven activation of BK channels. J Physiol 545: 933-944.
14. Shimizu H, Oh I, Okada S, Mori M (2005) Inhibition of appetite by nasal leptin administration in rats. Int J Obes Relat Metab Disord 29: 858-863.
15. Stables J P, Bertram E H, White H S, Coulter D A, Dichter M A, Jacobs M P, Loscher W, Lowenstein D H, Moshe S L, Noebels J L, Davis M (2002) Models for epilepsy and epileptogenesis: report from the NIH workshop, Bethesda, Md. Epilepsia 43: 1410-1420.
16. Thio L L, Shanmugam A, Isenberg K, Yamada K (2003) Benzodiazepines block alpha2-containing inhibitory glycine receptors in embryonic mouse hippocampal neurons. J Neurophysiol 90: 89-99.
17. Thio L L, Wong M, Yamada K A (2000) Ketone bodies do not directly alter excitatory or inhibitory hippocampal synaptic transmission. Neurology 54: 325-331.
18. Wong M, Ess K C, Uhlmann E J, Jansen L A, Li W, Crino P B, Mennerick S, Yamada K A, Gutmann D H (2003) Impaired glial glutamate transport in a mouse tuberous sclerosis epilepsy model. Ann Neurol 54: 251-256.
19. Yang X F, Rothman S M (2001) Focal cooling rapidly terminates experimental neocortical seizures. Ann Neurol 49: 721-726.

What is claimed is:

1. A method of inhibiting seizures in a subject in need thereof, the method comprising intranasally administering a composition comprising leptin to the subject in need of treatment for seizures, wherein leptin is the mature protein product of the obese (ob) gene of the subject, such that brain leptin levels in the subject are increased to greater than 15 pg/mg of total brain protein, and seizures in the subject are inhibited.

2. The method of claim 1, wherein the seizures are focal or general seizures.

3. The method of claim 1, wherein the subject is human.

4. A method of inhibiting seizures in a subject in need thereof, the method comprising:
   (a) determining the therapeutically effective amount of leptin required to increase brain leptin levels to greater than 15 pg/mg total brain protein in the subject in need of treatment for seizures, and
   (b) administering the therapeutically effective amount of a composition comprising leptin to the subject in need of treatment for seizures, wherein leptin is the mature protein product of the obese (ob) gene of the subject, such that the brain leptin levels are increased to greater than 15 pg/mg total brain protein in the subject, thereby inhibiting seizures in the subject.

5. The method of claim 4, wherein the brain leptin levels are increased to greater than 20 pg/mg in the subject.

6. The method of claim 4, wherein the composition is administered mucosally.

7. The method of claim 4, wherein the composition is administered intranasally.

* * * * *